(12) United States Patent
Wang et al.

(10) Patent No.: US 11,662,606 B2
(45) Date of Patent: May 30, 2023

(54) ORTHOKERATOLOGY LENS AND METHOD FOR MAKING ORTHOKERATOLOGY LENSES

(71) Applicant: EYEBRIGHT MEDICAL TECHNOLOGY (BEIJING) CO., LTD., Beijing (CN)

(72) Inventors: Zhao Wang, Beijing (CN); Jiangbing Xie, Beijing (CN)

(73) Assignee: EYEBRIGHT MEDICAL TECHNOLOGY (BEIJING) CO., LTD., Beijing (CN)

( * ) Notice: Subject to any disclaimer, the term of this patent is extended or adjusted under 35 U.S.C. 154(b) by 484 days.

(21) Appl. No.: 16/770,314

(22) PCT Filed: Nov. 30, 2018

(86) PCT No.: PCT/CN2018/118438
§ 371 (c)(1),
(2) Date: Jun. 5, 2020

(87) PCT Pub. No.: WO2019/109862
PCT Pub. Date: Jun. 13, 2019

(65) Prior Publication Data
US 2021/0181529 A1    Jun. 17, 2021

(30) Foreign Application Priority Data

Dec. 6, 2017  (CN) .......................... 201711276716.4
Dec. 6, 2017  (CN) .......................... 201711278012.0
(Continued)

(51) Int. Cl.
*G02C 7/04*     (2006.01)
*B29D 11/00*    (2006.01)

(52) U.S. Cl.
CPC ........ *G02C 7/047* (2013.01); *B29D 11/00105* (2013.01)

(58) Field of Classification Search
CPC .......................... G02C 7/047; B29D 11/00105
(Continued)

(56) References Cited

U.S. PATENT DOCUMENTS 6,010,219 A * 1/2000 Stoyan ................... G02C 7/047
                                                351/159.23
6,296,867 B1 * 10/2001 Peyman ............... A61K 9/0051
                                                525/200
(Continued)

FOREIGN PATENT DOCUMENTS

CN      1672085 A    9/2005
CN      2914127 Y    6/2007
(Continued)

OTHER PUBLICATIONS

International Search Report for International Application No. PCT/CN2018/118438, dated May 30, 2019.
(Continued)

*Primary Examiner* — James R Greece
(74) *Attorney, Agent, or Firm* — Cantor Colburn LLP

(57) ABSTRACT

The present disclosure relates to an orthokeratology lens which may comprise an inner surface facing a cornea of a human eye when the orthokeratology lens is worn and an outer surface opposite the inner surface, the inner surface comprising a centrally located base arc zone, wherein the base arc zone is configured for pressing and shaping an anterior surface of the cornea to have a shape that conforms to the base arc zone, wherein the base arc zone comprises two or more regions, at least two of the two or more regions having different radii of curvature. The present disclosure also relates to a method for making orthokeratology lenses.

34 Claims, 8 Drawing Sheets

(30) Foreign Application Priority Data

Dec. 6, 2017 (CN) .......................... 201721682214.7
Nov. 26, 2018 (CN) .......................... 201811416151.X
Nov. 26, 2018 (CN) .......................... 201821953457.4

(58) Field of Classification Search
USPC ........................................ 351/159.02, 159.23
See application file for complete search history.

(56) References Cited

U.S. PATENT DOCUMENTS

| | | | | |
|---|---|---|---|---|
| 8,388,130 | B2* | 3/2013 | Legerton | G02C 7/044 |
| | | | | 351/159.23 |
| 8,500,273 | B2* | 8/2013 | Tung | G02C 7/047 |
| | | | | 351/159.79 |
| 8,801,175 | B2* | 8/2014 | Legerton | B29D 11/00038 |
| | | | | 351/159.23 |
| 2005/0213029 | A1 | 9/2005 | Meyers | |
| 2006/0152673 | A1* | 7/2006 | Cotie | G02C 7/047 |
| | | | | 351/159.34 |
| 2006/0290882 | A1* | 12/2006 | Meyers | G02C 7/049 |
| | | | | 351/159.62 |
| 2009/0237612 | A1* | 9/2009 | Cotie | G02C 7/047 |
| | | | | 351/159.37 |
| 2010/0128224 | A1 | 5/2010 | Legerton | |
| 2013/0182215 | A1 | 7/2013 | Tung | |
| 2014/0132915 | A1* | 5/2014 | Gemoules | A61B 3/107 |
| | | | | 351/159.23 |
| 2021/0181529 | A1* | 6/2021 | Wang | A61F 9/013 |

FOREIGN PATENT DOCUMENTS

| | | | |
|---|---|---|---|
| CN | 102472899 A | 5/2012 | |
| CN | 102047172 B | 10/2012 | |
| CN | 104849875 A | 8/2015 | |
| CN | 105785591 A | 7/2016 | |
| CN | 105974605 A | 9/2016 | |
| CN | 106461971 A | 2/2017 | |
| CN | 106932920 A | 7/2017 | |
| CN | 107728338 A | 2/2018 | |
| CN | 108008544 A | 5/2018 | |
| CN | 208092366 U | 11/2018 | |
| WO | WO-2013101793 A1 * | 7/2013 | ............. G02C 7/041 |

OTHER PUBLICATIONS

CNIPA Office Action for corresponding CN Application No. 201711276716.4; dated Jan. 20, 2023.

* cited by examiner

ORTHOKERATOLOGY LENS AND METHOD FOR MAKING ORTHOKERATOLOGY LENSES

CROSS REFERENCE TO RELATED APPLICATIONS

This is the U.S. national stage of application No. PCT/CN2018/118438, filed on Nov. 30, 2018. Priority under 35 U.S.C. § 119(a) and 35 U.S.C. § 365(b) is claimed from Chinese Application Nos. 201711278012.0, 201711276716.4, and 201721682214.7, filed Dec. 6, 2017; and Chinese Application Nos. 201811416151.X and 201821953457.4 filed on Nov. 26, 2018, the disclosure of which is also incorporated herein by reference.

FIELD OF THE INVENTION

The present disclosure relates to an orthokeratology lens, and more particularly to an orthokeratology lens having a base arc zone with more than one radius of curvature. The present disclosure also relates to a method for making orthokeratology lenses.

BACKGROUND

Presbyopia is a visual problem inevitably suffered by people of middle and old age. With age, accommodative ability of the eye gradually decreases, causing difficulty in near vision for the patient, so that when working at near distances, a convex lens must be used in addition to the static refractive correction for clear near vision, which is known as presbyopia. With improvement of living standard of modern people, especially beauty-conscious women of middle age, their requirements on personal appearance are increasingly increased, people want to keep a young state at any time and do not want to expose presbyopia situation of themselves, and the problem caused by presbyopia is more and more serious. Currently, presbyopia is mainly addressed by wearing presbyopic glasses, undergoing surgical operations, wearing multifocal contact lenses and the like. External wearing such as wearing presbyopic glasses or contact lenses worn in the daytime have problems in the aspects of convenience, correction effect and correction stability, and particularly, wearing presbyopic glasses seriously influences appearance of a wearer. Surgical operation mainly refers to cornea implantation or various multifocal intraocular lenses implantation. These kinds of corrections are all irreversible, causing damages to eye tissues and various problems with respect to safety, and most people of this age generally enter the stage of high incidence of cataract and are subjected to other subsequent eye treatments, such as cataract surgical operations and the like, and the surgical operations bring serious troubles to the subsequent surgical operations. Therefore, a hidden, effective and safe measure for correcting presbyopia is urgently needed.

The avascular, transparent, fibrous membrane at one sixth of the anterior end of the eye wall is called cornea. Normal cornea is highly transparent and histologically divided into five layers from front to back: an epithelial cell layer, a front elastic layer, a matrix layer, a back elastic layer, and an endothelial cell layer. The epithelial cell layer is rich in sensory nerve endings, is the barrier of the cornea, can regenerate and can deform. Orthokeratology lens is a lens made of rigid air-permeable material, is worn at night, and applies pressing force through eyelid-orthokeratology lens-cornea to promote migration/deformation of cornea epithelial cells and change radius of curvature of the cornea (lens), thereby changing refractive power of the cornea, temporarily changing shape of the cornea and correcting ametropia. This is a reversible, non-operative refractive correction product, usually in night-worn mode (worn at night during sleep, taken off in daytime), the wearer believes that their ametropia problem is "cured" and is not constrained by any external conditions during daytime. It does not bring any additional trouble compared to other means of vision correction, being a very excellent means of vision correction.

The principle of refractive correction of the orthokeratology lens is fundamentally different from that of a common contact lens. The orthokeratology lens is worn at night, the optical zone does not play any optical role, but the anterior surface of the cornea is molded into the shape of the rear surface (also called base arc zone) of the optical zone of the orthokeratology lens through wearing for a certain time, so that the refractive power of the cornea is changed, and the function of refractive correction is realized. If the base arc zone of the orthokeratology lens is made flatter than the cornea flat axis radius of curvature, the orthokeratology lens has the function of correcting myopia; if the base arc zone of the orthokeratology lens is made steeper than the cornea flat axis radius of curvature, the orthokeratology lens can be used for correcting hyperopia.

The orthokeratology lens is developed in several stages and is divided into a plurality of designs such as a three-arc-zone design, a four-arc-zone design, a multi-arc-zone design and the like. Design for base arc zone is consistent in any stage of design and is a section of continuous arc, and other arc sections jointly form a geometric design, help the base arc to press and shape the cornea, so that the resultant force generated by hydrodynamic force generated between inner surface of the lens, tears and cornea epithelium, mechanical pressing of the lens and movement of eyelids can apply force to the central region of the cornea. The orthokeratology lens is generally divided into four zones, namely a base arc zone, a reversal arc zone, an adaptive arc zone and a peripheral arc zone. FIG. 1 shows a schematic diagram of an orthokeratology lens, where BC is base arc zone, RC is reversal arc zone, AC is the adaptive arc zone, and PC is an optional peripheral arc zone. The orthokeratology lens may also be provided without a peripheral arc zone, such as certain orthokeratology lenses of three-arc-zone design, where the adaptive arc zone is integral with the peripheral arc zone to form a straight arc.

Base arc zone is the main treatment area of the orthokeratology lens. Base arc zone of traditional orthokeratology lenses is designed as a spherical surface, and the radius of curvature of the base arc zone is designed in accordance with patient's degree-decreasing requirement. Most of the existing orthokeratology lenses are designed for correcting myopia. During clinical use, it is found that some patients wearing the orthokeratology lens can form myopic peripheral defocusing to control growth of ocular axis, and the orthokeratology lens is therefore mostly used for correcting and controlling myopia of young people. WO2004/015479 discloses an orthokeratology lens for correcting hypermetropia, wherein the base arc zone of the orthokeratology lens is steeper than the cornea flat axis.

Hyperopia is fundamentally different from presbyopia. Hyperopia represents ametropia, and presbyopia represents loss of accommodation. The presbyopic patient needs to realize the near-vision function under the condition of ensuring the clear far vision. At present, no orthokeratology lens can serve the purpose of correcting presbyopia.

However, the cornea is an elastic body, the deformation characteristics occurred in the plastic process accord with the deformation characteristics of the elastic body. When the cornea is deformed after being pressed by external force, the total volume of the cornea is constant, and the surface shape is gradually changed. Stress of the cornea under the pressure of an orthokeratology lens is unequal, with stress at the center being the highest, and gradually weakened outwards. These features all result in the final cornea not being completely conformed to the base arc zone of the orthokeratology lens, thereby affecting the final presbyopia correction. For the existing orthokeratology lenses, the following problems mainly exist: (1) the deformation characteristic of the elastomer cannot present too frequent radius of curvature change in a small range, and over-design of optical partition for base arc zone cannot realize differentiation of a myopia shaping region and a presbyopia shaping region; (2) the design of sector-shaped regions and the design of asymmetric regions have the difficulty of position alignment, and the shaping regions cannot be ensured to be in the same position at each time the orthokeratology lens is worn, so that the shaping fails; (3) the deformation characteristic of the elastomer under pressure is ignored, if the cornea is desired to be raised as an elastic body at a certain position, specifically, if the presbyopia correction region of the cornea is to be raised, the cornea must be subjected to a pressing force on both sides of the presbyopia correction region, and the shaping fails due to the asymmetrical design of the pressure, for example, the pressure applied to both sides of the presbyopia correction region is lower on one side and higher on the other side, or the pressure is applied to only one side, which causes the presbyopia correction region to be not successfully raised; (4) after the cornea is shaped, the shape is gradually deformed, and an excessively large central region diameter (e.g., greater than 1.75 mm) can cause a region peripheral to the central region (typically a presbyopia correction region) to extend beyond the outer edge of the pupil, losing the correction ability of the presbyopia correction region.

SUMMARY

In a first aspect of the present disclosure, there is provided an orthokeratology lens comprising an inner surface facing a cornea of a human eye when the orthokeratology lens is worn and an outer surface opposite the inner surface, the inner surface comprising a centrally located base arc zone, wherein the base arc zone is configured for pressing and shaping an anterior surface of the cornea to have a shape that conforms to the base arc zone, wherein the base arc zone comprises two or more regions, at least two of the two or more regions having different radii of curvature.

In an embodiment of the first aspect, the two or more regions of the base arc zone comprise a centrally located circular central region and one or more concentric annular regions surrounding the central region.

In an embodiment of the first aspect, the radii of curvature of the two or more regions of the base arc zone alternate in a radial direction.

In an embodiment of the first aspect, the radii of curvature of the two or more regions of the base arc zone gradually decrease outwards from the center.

In an embodiment of the first aspect, the central region has a diameter greater than 1 mm, and preferably greater than 2 mm.

In an embodiment of the first aspect, the two or more regions of the base arc zone are two or more sector-shaped regions, and the two or more sector-shaped regions collectively make up the base arc zone.

In an embodiment of the first aspect, the two or more regions of the base arc zone are two or more sector-shaped regions, the base arc zone further comprises a smooth transition region between each two adjacent sector-shaped regions, and wherein the two or more sector-shaped regions and the smooth transition regions collectively make up the base arc zone.

In an embodiment of the first aspect, the two or more regions of the base arc zone are irregularly shaped.

In an embodiment of the first aspect, the two or more regions of the base arc zone are a first region located in the middle and a second region and a third region located on either side of the first region, and the first region, the second region and the third region collectively make up the base arc zone.

In an embodiment of the first aspect, the two or more regions of the base arc zone are a first region located in the middle and a second region and a third region located on either side of the first region, the base arc zone further comprises a first smooth transition region located between the first region and the second region and a second smooth transition region located between the first region and the third region, and wherein the first region, the second region, the third region, the first smooth transition region and the second smooth transition region collectively make up the base arc zone.

In an embodiment of the first aspect, the two or more regions of the base arc zone are a first region that is a part of a circular ring and a second region that has a complete circular portion in its center, and wherein the first region and the second region collectively make up the base arc zone.

In an embodiment of the first aspect, the two or more regions of the base arc zone are a first region that is a part of a circular ring and a second region that has a complete circular portion in its center, the base arc zone further comprises a smooth transition region located between the first region and the second region, and wherein the first region, the second region and the smooth transition region collectively make up the base arc zone.

In an embodiment of the first aspect, $\Delta T$ calculated from the following equation is from +0.5 D to +5.0 D, preferably from +0.75 D to +3.5 D, and more preferably from +1.0 D to +3.0 D:

$$\Delta T = 1000 * (n-1)\left(\frac{1}{R_2} - \frac{1}{R_1}\right)$$

where $R_1$ is the maximum radius of curvature of the base arc zone in millimeters, $R_2$ is the minimum radius of curvature of the base arc zone in millimeters, n is the refractive index of the cornea with a value of 1.3375.

In an embodiment of the first aspect, the base arc zone has a maximum radius of curvature of 6.0 mm to 10.5 mm, and preferably 7.0 mm to 10.0 mm.

In an embodiment of the first aspect, the base arc zone has a minimum radius of curvature of 5.51 mm to 10.34 mm, preferably 5.65 mm to 9.85 mm, and more preferably 6.53 mm to 9.71 mm.

In an embodiment of the first aspect, the base arc zone has a diameter of 4.5 mm to 7.0 mm, preferably 5.0 mm to 6.8 mm, and more preferably 5.2 mm to 6.5 mm.

In an embodiment of the first aspect, the base arc zone is circular.

In an embodiment of the first aspect, the base arc zone is elliptical.

In a second aspect of the present disclosure, there is provided a method for making an orthokeratology lens comprising an inner surface facing a cornea of a human eye when the orthokeratology lens is worn and an outer surface opposite the inner surface, the inner surface comprising a centrally located base arc zone, the method comprising the steps of:

(a) determining the maximum radius of curvature of the base arc zone;

(b) determining an amount of presbyopia correction required by the wearer;

(c) determining the minimum radius of curvature of the base arc zone using the following equation:

$$\frac{1000*(n-1)}{R1} + \Delta T = \frac{1000*(n-1)}{R2}$$

where n is a refractive index of the cornea, R1 is the maximum radius of curvature of the base arc zone in millimeters, ΔT is the determined amount of presbyopia correction required by the wearer in D (diopter), R2 is the minimum radius of curvature of the base arc zone in millimeters; and (d) making an orthokeratology lens such that the base arc zone comprises two or more regions, and such that a first region of the two or more regions has the maximum radius of curvature and a second region of the two or more regions has the minimum radius of curvature.

In an embodiment of the second aspect, step (a) comprises:

(a1) determining a refractive index of the cornea;

(a2) determining an original radius of curvature of an anterior surface of the cornea of the wearer;

(a3) determining an amount of ametropia correction required by the wearer;

(a4) determining the maximum radius of curvature of the base arc zone using the following equation:

$$\frac{1000*(n-1)}{R} + \Delta K = \frac{1000*(n-1)}{R1}$$

where n is the determined refractive index of the cornea, R is the determined original radius of curvature of the anterior surface of the cornea of the wearer in millimeters, ΔK is the determined amount of ametropia correction in D (diopter), and R1 is the maximum radius of curvature of the base arc zone in millimeters.

In an embodiment of the second aspect, the method further comprises the steps of:

(e) determining a mid-range additional refractive power required by the wearer;

(f) determining an intermediate radius of curvature of the base arc zone using the following equation:

$$\frac{1000*(n-1)}{R1} + \Delta T' = \frac{1000*(n-1)}{R3}$$

where n is a refractive index of the cornea, R1 is the determined maximum radius of curvature of the base arc zone in millimeters, ΔT' is the determined mid-range additional refractive power in D (diopter), and R3 is the intermediate radius of curvature of the base arc zone in millimeters; and wherein the step (d) further comprises making the orthokeratology lens such that a third region of the two or more regions has the intermediate radius of curvature.

In an embodiment of the second aspect, step (e) comprises determining the mid-range additional refractive power required by the wearer using the following equation:

$$\Delta T' = \frac{1000}{M'}$$

where ΔT' is the mid-range additional refractive power required by the wearer in D (diopter), namely the amount of presbyopia correction required for mid-range vision, and M' is a visual distance for mid-range vision of the wearer on the basis of appropriate correction of far vision in millimeters.

In an embodiment of the second aspect, step (b) comprises determining the amount of presbyopia correction required by the wearer using the following equation:

$$\Delta T = \frac{1000}{M}$$

where ΔT is the amount of presbyopia correction required by the wearer in D (diopter), and M is the nearest distance that the wearer can achieve for near vision on the basis of appropriate correction of far vision in millimeters.

In a third aspect of the present disclosure, there is provided an orthokeratology lens comprising an inner surface facing a cornea of a human eye when the orthokeratology lens is worn and an outer surface opposite the inner surface, the inner surface comprising a centrally located base arc zone, wherein the base arc zone comprises a centrally located circular first region, a circular ring shaped second region surrounding the first region, and a third region surrounding the second region, wherein a radius of curvature of the second region is smaller than a radius of curvature of the first region, and the radius of curvature of the second region is smaller than a radius of curvature of the third region.

In an embodiment of the third aspect, the first region and the third region have the same radius of curvature.

In an embodiment of the third aspect, the radii of curvature of the first region and the second region satisfy the following relationship:

$$0.5 \leq 337.5*\left(\frac{1}{R_B} - \frac{1}{R_A}\right) \leq 6.0$$

where $R_A$ is the radius of curvature of the first region in millimeters and $R_B$ is the radius of curvature of the second region in millimeters.

In an embodiment of the third aspect, the radii of curvature of the first region and the third region are 6.0 mm to 10.5 mm, and preferably 7.0 mm to 10.0 mm.

In an embodiment of the third aspect, the radius of curvature of the second region is 5.42 mm to 10.34 mm, and preferably 6.22 mm to 9.85 mm.

In an embodiment of the third aspect, the base arc zone is circular.

In an embodiment of the third aspect, the base arc zone has a diameter of 4.5 mm to 8.0 mm, preferably 5.0 mm to 7.0 mm, and more preferably 5.2 mm to 6.5 mm.

In an embodiment of the third aspect, the first region has a diameter of 0.50 mm to 1.75 mm, preferably 0.50 mm to 1.5 mm, and more preferably 1.0 mm.

In an embodiment of the third aspect, the second region has a radial width of 0.75 mm to 1.5 mm, preferably 1.0 mm to 1.25 mm, and more preferably 1.0 mm.

In an embodiment of the third aspect, the third region has a radial width of 0.75 mm to 3.0 mm, preferably 1.0 mm to 2.0 mm, and more preferably 1.0 mm to 1.75 mm.

In an embodiment of the third aspect, the base arc zone is elliptical.

The present disclosure has at least the following advantages.

(1) The orthokeratology lens in accordance with the present disclosure or the orthokeratology lens made by the method in accordance with the present disclosure has a base arc zone with more than one radius of curvature, so that the cornea can form more than one focal point after being shaped, the lens is worn at night and is taken off in the daytime, realizing a combination correction of ametropia and presbyopia, and it is convenient, attractive and effective and more conforms to the pursuit of modern people on the quality of life.

(2) For common frame presbyopic glasses and common multifocal contact lenses, the glasses/lenses cannot keep synchronization with eyeballs, and after wearing the glasses/lenses, a patient needs to continuously adjust the glasses/lenses in accordance with positions of the glasses/lenses and positions of the objects to be watched, or may suffer from glare, blurred vision and dizziness when the glasses/lenses are not centered. When the orthokeratology lens is worn, the orthokeratology lens is inherently centered, and no matter which direction a user looks at, blurred vision and inapplicability caused by the position change of the lens can be avoided.

(3) Patients with presbyopia are older and most of them enter the stage of high incidence of cataract. The orthokeratology lens in accordance with the present disclosure provides reversible correction based on activities of cornea cells, and after stopping using the orthokeratology lens for a period of time, the cornea can be restored to its original state without any damage, so that the orthokeratology lens is convenient for patients to perform subsequent other eye treatments, and is safer compared with an surgical operation.

Definition of Terms

The following definitions apply to the terms used in this specification unless otherwise specified.

Base arc zone (BC) is the most central part of the orthokeratology lens and is the inner surface of the optical zone and is used for pressing and shaping the anterior surface of the cornea into the shape of the base arc zone, and the region of the cornea after shaping is the optical zone and plays the role of optical imaging.

Reverse arc zone (RC) is a second zone closely connected with the base arc zone, and has the function of connecting the base arc zone and the adaptive arc zone, forming a gap between the orthokeratology lens and the anterior surface of the cornea, and storing and promoting circulation of tears.

Adaptive arc zone (AC) is also called a positioning arc zone, a matching arc zone and the like, is immediately adjacent to the reversal arc zone, and the adaptive arc zone is matched with the shape of the cornea to play a role of positioning.

Peripheral arc zone (PC) is optional, is positioned at the outermost edge of the orthokeratology lens, is closely connected with the adaptive arc zone, is generally flatter than the adaptive arc zone, and presents a certain tilting angle with the surface of the cornea, thereby ensuring exchange and circulation of tears and oxygen around the cornea and the orthokeratology lens.

Near vision refers to watching vicinity, generally about 30 cm away from the eye, and corresponds to near vision ability.

Far vision refers to watch distantly, generally about 5 m away from the eyes, and corresponds to far vision ability.

Mid-range vision refers to watching at a distance between near and far, generally about 30 cm to 5 m away from the eye, and corresponds to mid-range vision ability.

Radial width refers to the width in the radial direction.

Furthermore, unless defined otherwise, all technical and scientific terms used herein have the same meaning as commonly understood by one of ordinary skill in the art to which this disclosure pertains. In the event of inconsistencies, the present specification and the definitions included therein will prevail.

DETAILED DESCRIPTION OF EMBODIMENTS

The following specific embodiments are provided only for further illustration of the present disclosure, and the present disclosure is not limited to the following specific embodiments. Any variations on these embodiments, which are within the spirit and scope of the principles of this disclosure, are intended to be within the scope of protection of the present disclosure.

The refractive state of the cornea is primarily determined by its radius of curvature. In practical clinical application, a common conversion relationship between the radius of curvature of the cornea and the refractive power of the cornea is as follows:

$$K = \frac{1000*(n-1)}{R} \quad (1)$$

where K is the refractive power of the cornea in D (diopter), R is the radius of curvature of the anterior surface of the cornea in millimeters, and n is the refractive index of the cornea. For example, n may be 1.3375.

Figure 1:
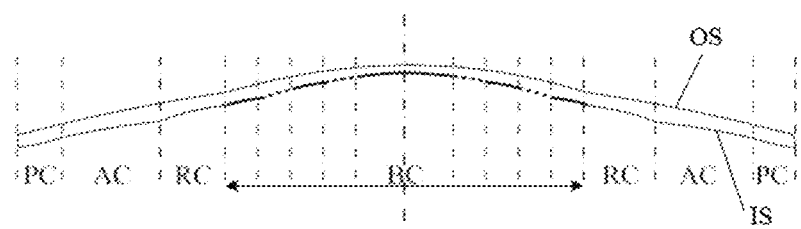
FIG. 1 schematically illustrates a cross-sectional side view of an orthokeratology lens.

As shown in FIG. 1, the orthokeratology lens includes an inner surface IS facing the cornea of the human eye when the orthokeratology lens is worn and an outer surface OS opposite the inner surface. The inner surface IS of the orthokeratology lens includes a centrally located base arc zone BC. When the orthokeratology lens is worn, the base arc zone BC of the orthokeratology lens is in contact with the anterior surface of the cornea of a human eye. When a patient (also called a wearer) has ametropia, the radius of curvature of the anterior surface of the cornea of the human eye, that is, R in the above equation (1), is adjusted by the base arc zone BC of the orthokeratology lens, so that correction of ametropia of the human eye can be achieved. In the following FIG. 2, FIG. 3A-FIG. 3B, FIG. 4A-FIG. 4B and FIG. 5A-FIG. 5D, the base arc zone BC is shown as circular. However, in some embodiments, the base arc zone BC may have other shapes as well, such as elliptical, oval, and the like.

As known to those skilled in the art, the inner surface IS of the orthokeratology lens may further include an annular reversal arc zone RC located radially outward of the base arc zone BC and an annular adaptive arc zone AC located radially outward of the reversal arc zone RC. The inner surface IS of the orthokeratology lens may also include an annular peripheral arc zone PC located radially outward of the adaptive arc zone AC.

The base arc zone assumes a therapeutic role and its design is related to the original shape of the wearer's cornea, the wearer's refractive condition. The radius of curvature of the base arc zone is calculated by a refractive calculation formula from the original shape of the wearer's cornea (primarily the radius of curvature) and the amount of refractive correction required.

The other zones (the reversal arc zone, the adaptive arc zone and the peripheral arc zone) outside the base arc zone mainly play roles in positioning and promoting circulation of tears, and assist in the stable shaping of the base arc zone. The shape of the adaptive arc zone is matched with that of the cornea at the corresponding position, so that the lens is well attached, and the position of the lens is stabilized. The parameters of the adaptive arc zone are determined by a try-on method of a try-on piece. The parameters of the adaptive arc zone are determined by accurately measuring the cornea surface shape so as to be matched with the surface shape measurement results.

In one aspect of the present disclosure, the present disclosure innovatively provides a method for making an orthokeratology lens having a base arc zone with at least two different radii of curvature such that a human eye, after wearing the orthokeratology lens, creates at least two focal points in a cornea optical zone, thereby allowing a wearer's ametropia and presbyopia to be corrected simultaneously.

The method for making an orthokeratology lens of the present disclosure is similar to the prior art in determining the parameters of the other auxiliary zones. Specifically, first, eye parameters of the wearer are measured, and in some embodiments, corneal morphology, mainly including radii of curvature of the cornea in all directions, astigmatism, aspheric coefficients, etc., is determined by using a corneal topographer, keratometer, or other detection device. On the basis of the measured parameters, parameters of the auxiliary zones of the wearer except the base arc zone are determined by repeatedly fitting and evaluating a try-on piece with known parameters. Or fitting conditions of the auxiliary zones are determined through software simulation, and then the parameters of the auxiliary zones are determined.

The base arc zone of the existing orthokeratology lens only has the function of refractive correction and comprises only one radius of curvature. The orthokeratology lens made by the methods of the present disclosure has a base arc zone with more than one radius of curvature. In accordance with the method of the present disclosure, first, the maximum radius of curvature of the base arc zone is determined; then, based on the determined maximum radius of curvature of the base arc zone and an amount of presbyopia correction required by the wearer, the minimum radius of curvature of the base arc zone is calculated by a refractive calculation formula, wherein the amount of presbyopia correction required by the wearer can be determined by optometry, try-on, or the like.

When the wearer has ametropia, radius of curvature of an anterior surface of the cornea is adjusted through the base arc zone of the orthokeratology lens, and ametropia correction is achieved.

In the method of the present disclosure, the maximum radius of curvature of the base arc zone may be determined in a variety of ways, such as lens try-on, software simulation, mathematical calculations, and the like.

In an embodiment, a plurality of try-on pieces of the orthokeratology lens (various parameters of the base arc zone of these try-on pieces of the orthokeratology lens are known) can be worn by a wearer, and if a certain try-on piece enables the far vision of the wearer to be appropriately corrected, the radius of curvature of the base arc zone of this try-on piece is determined as the maximum radius of curvature of the base arc zone of the orthokeratology lens to be made by the present disclosure.

In another embodiment, the corneal topography of a wearer may be measured using a corneal topographer, the amount of ametropia correction required by the wearer may be determined using optometry equipment, and then the maximum radius of curvature of the base arc zone of the orthokeratology lens to be made by the present disclosure may be determined using sagittal height calculations. For example, the amount of ametropia correction required by the wearer is determined as $\Delta K$, the sagittal height of the original cornea of the patient at the radius r is determined as h, the sagittal height difference to be resulted from the amount of ametropia correction $\Delta K$ is $\Delta h$, so the region of the base arc zone which comprises the maximum radius of curvature has a sagittal height at the radius r: $h'=h+\Delta h$. Then, the sagittal height is converted into the maximum radius of curvature R1 of the base arc zone of the orthokeratology lens by using the following equation:

$$R1 = \frac{r^2 - h'^2}{2h'}.$$

In another embodiment, the maximum radius of curvature of the base arc zone of the orthokeratology lens to be made by the present disclosure may be determined based on the original radius of curvature and the amount of ametropia correction of the anterior surface of the cornea of the wearer, wherein the original radius of curvature and the amount of ametropia correction of the anterior surface of the cornea of the wearer may be measured by a computer refractometer, optometry, or the like.

For example, the maximum radius of curvature of the base arc zone may be determined in accordance with the following equation:

$$K + \Delta K = \frac{1000*(n-1)}{R1} \qquad (2)$$

combining with equation (1) to obtain:

$$\frac{1000*(n-1)}{R} + \Delta K = \frac{1000*(n-1)}{R1} \qquad (3)$$

where n is the refractive index of the cornea, R is the original radius of curvature of the anterior surface of the cornea of the wearer in millimeters, $\Delta K$ is the amount of ametropia correction in D (diopter), and R1 is the maximum radius of curvature of the base arc zone in millimeters.

In the method of the present disclosure, the minimum radius of curvature of the base arc zone is determined in accordance with the following equation:

$$K + \Delta K + \Delta T = \frac{1000*(n-1)}{R2} \qquad (4)$$

combining with equation (2) to obtain:

$$\frac{1000*(n-1)}{R1} + \Delta T = \frac{1000*(n-1)}{R2} \qquad (5)$$

where n is the refractive index of cornea, R1 is the maximum radius of curvature of base arc zone in millimeters, $\Delta T$ is the amount of presbyopia correction required by the wearer in D (diopter), and R2 is the minimum radius of curvature of the base arc zone in millimeters.

In the methods of the present disclosure, the base arc zone of the orthokeratology lens made in accordance with the method of the present disclosure includes two or more regions. A first region of the two or more regions of the base arc zone has a maximum radius of curvature and a second region of the two or more regions of the base arc zone has a minimum radius of curvature. Surface shapes of the two or more regions of the base arc zone can be spherical surfaces or aspheric surfaces, or the surface shape(s) of a part of the two or more regions can be spherical surface(s) and the surface shape(s) of the rest of the two or more regions can be aspheric surface(s).

In some embodiments, the base arc zone of the orthokeratology lens made by the method of the present disclosure may include one or more intermediate radii of curvature in addition to the maximum radius of curvature and the minimum radius of curvature, depending on the wearer's presbyopia, thereby allowing the wearer to develop one or more mid-range vision between near and far vision.

The intermediate radius of curvature is determined in a similar manner to the minimum radius of curvature. In the method of the present disclosure, the intermediate radius of curvature of the base arc zone is determined in accordance with the following equation:

$$K + \Delta K + \Delta T' = \frac{1000*(n-1)}{R3} \quad (6)$$

combining with equation (2) to obtain:

$$\frac{1000*(n-1)}{R1} + \Delta T' = \frac{1000*(n-1)}{R3} \quad (7)$$

where n is the refractive index of the cornea, R1 is the maximum radius of curvature of the base arc zone in millimeters, $\Delta T'$ is the additional refractive power (also called mid-range additional refractive power) required by the mid-range vision of the wearer in D (diopter), and R3 is the intermediate radius of curvature of the base arc zone in millimeters.

In some embodiments, a third region of the two or more regions of the base arc zone of the orthokeratology lens made in accordance with the method of the present disclosure has the intermediate radius of curvature.

In some embodiments, the amount of presbyopia correction required by the wearer is determined based on the degree of presbyopia of the wearer. If M is the nearest distance that the wearer can achieve for near vision on the basis of appropriate correction of far vision in millimeters, the amount of presbyopia correction required by the wearer is as follows:

$$\Delta T = \frac{1000}{M} \quad (8)$$

The amount of presbyopia correction of normal eye $\Delta T$ is generally from +0.5 D to +5.0 D.

In the method of the present disclosure, the mid-range additional refractive power is determined in a manner similar to that of the amount of presbyopia correction desired by the wearer. In some embodiments, the mid-range additional refractive power required by the wearer is determined from a visual distance for mid-range vision of the wearer. If M' is the visual distance for mid-range vision of the wearer on the basis of appropriate correction of far vision in millimeters, the mid-range additional refractive power required by the wearer is:

$$\Delta T' = \frac{1000}{M'} \quad (9)$$

The present disclosure innovatively provides that the base arc zone of the orthokeratology lens has at least two different radii of curvature, so that the human eye can generate at least two focal points in the optical zone of the cornea after wearing the orthokeratology lens, thereby correcting the ametropia and the presbyopia of the patient simultaneously.

Figure 2:
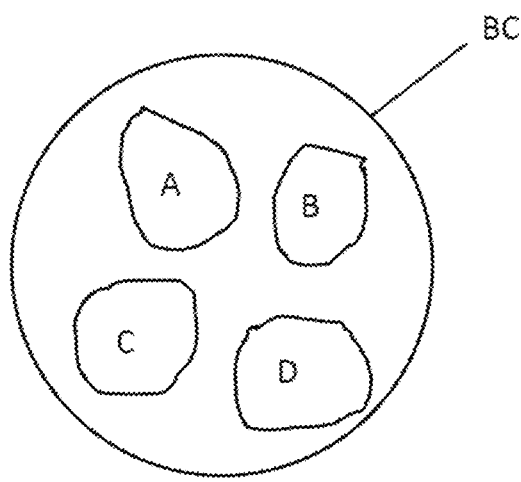
FIG. 2 schematically illustrates the base arc zone of an orthokeratology lens in accordance with the present disclosure.

In another aspect of the disclosure, there is provided an orthokeratology lens. In the orthokeratology lens in accordance with the present disclosure, the base arc zone comprises two or more regions. At least two of the two or more regions of the base arc zone have different radii of curvature. The surface shapes of two or more regions of the base arc zone can be spherical surfaces or aspheric surfaces, or the surface shape(s) of a part of the two or more regions can be spherical surface(s) and the surface shape(s) of the rest of the two or more regions can be aspheric surface(s). FIG. 2 shows that the base arc zone comprises four regions A, B, C and D. The four regions A, B, C and D can be of any shape as desired. At least two of the four regions A, B, C and D have different radii of curvature.

In some embodiments, the two or more regions of the base arc zone 100 comprise a centrally located circular central region $100_1$ and one or more concentric annular regions $100_2, 100_3, 100_4 \ldots$ surrounding the central region $100_1$.

In some embodiments, the radii of curvature of the two or more regions $100_1, 100_2, 100_3, 100_4 \ldots$ of the base arc zone 100 alternate in the radial direction. In particular, in some embodiments, the base arc zone 100 has two different radii of curvature that alternate in the radial direction, wherein regions $100_{2m-1}$ of the base arc zone 100 have a first radius of curvature and regions $100_{2m}$ of the base arc zone 100 have a second radius of curvature that is different from the first radius of curvature, wherein m is an integer greater than or equal to 1. In particular, in some embodiments, the base arc zone 100 has three different radii of curvature that alternate in the radial direction, wherein regions $100_{3m-2}$ of the base arc zone 100 have a first radius of curvature, regions $100_{3m-1}$ of the base arc zone 100 have a second radius of curvature that is different from the first radius of curvature, and regions $100_{3m}$ of the base arc zone 100 have a third radius of curvature that is different from the first radius of curvature and the second radius of curvature, wherein m is an integer greater than or equal to 1. Of course, in other embodiments, the base arc zone 100 may similarly have other numbers of different radii of curvature that alternate in the radial direction.

For example, in an embodiment, the orthokeratology lens 10 is made of a material that is highly oxygen permeable and rigid. The inner surface of the orthokeratology lens 10 comprises a base arc zone 100, a reversal arc zone, an adaptive arc zone, and a peripheral arc zone. The orthokeratology lens 10 has an overall diameter of 10.4 mm, with the base arc zone 100 having a diameter of 6.0 mm, the reversal arc zone having an inner diameter of 6.0 mm and an outer diameter of 7.8 mm. The adaptive arc zone has an inner diameter of 7.8 mm and an outer diameter of 9.4 mm. The peripheral arc zone has an inner diameter of 9.4 mm and an outer diameter of 10.4 mm. The orthokeratology lens 10 has a central thickness of 0.22 mm.

Figure 3A:
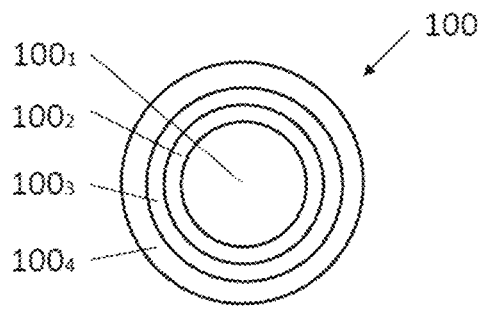
FIG. 3A schematically illustrates the base arc zone of an orthokeratology lens in accordance with a specific embodiment of the present disclosure.

In this embodiment, as shown in FIG. 3A, the base arc zone 100 comprises a central region $100_1$ and three concentric annular regions $100_2$, $100_3$ and $100_4$ surrounding the central region $100_1$. The central region $100_1$ has a diameter of 3 mm. The annular region $100_2$ has an inner diameter of 3 mm and an outer diameter of 4 mm. The annular region $100_3$ has an inner diameter of 4 mm and an outer diameter of 5 mm. The annular region $100_4$ has an inner diameter of 5 mm and an outer diameter of 6 mm. The radii of curvature of the regions $100_1$, $100_2$, $100_3$ and $100_4$ exhibit an alternating variation, wherein the radii of curvature of the central region $100_1$ and the annular region $100_3$ are the same, e.g. may be 8.88 mm, and the radii of curvature of the annular regions $100_2$ and $100_4$ are the same, e.g. may be 8.54 mm.

By wearing this orthokeratology lens 10, the cornea of a patient can provide a near focal point and a far focal point simultaneously after the orthokeratology lens 10 is removed. The refractive power of the cornea in those two regions corresponding to the central region $100_1$ and the annular region $100_3$ is 38.0 D, achieving myopia correction of −5.0 D, and thus clear far vision. The refractive power of the cornea in those two regions corresponding to the annular regions $100_2$ and $100_4$ is 39.5 D, adding a refractive power of +1.5 D to the far vision, thereby achieving presbyopia correction.

In the embodiment shown in FIG. 3A, the base arc zone comprises three concentric annular regions. Moreover, the base arc zone may comprise other numbers of concentric annular regions. In the embodiment shown in FIG. 3A, the regions of the base arc zone alternate with two different radii of curvature, providing two focal points. Moreover, the regions of the base arc zone may also alternate with more than two different radii of curvature, thereby providing more than two focal points. The diameter of the central region and the radial widths of the annular regions (i.e., half of the difference between the outer diameter and the inner diameter) can be adjusted in accordance with size of the patient's pupil, requirements for near vision clarity, etc.

In some embodiments, the radii of curvature of the two or more regions $100_1$, $100_2$, $100_3$ ... of the base arc zone 100 gradually decrease outwards from the center.

For example, in an embodiment, the orthokeratology lens 10 is made of a material that is highly oxygen permeable and rigid, comprising a base arc zone 100, a reversal arc zone, an adaptive arc zone, and a peripheral arc zone. The orthokeratology lens 10 has an overall diameter of 10.9 mm, with the base arc zone 100 having a diameter of 6.5 mm, the reversal arc zone having an inner diameter of 6.5 mm and an outer diameter of 8.3 mm. The adaptive arc zone has an inner diameter of 8.3 mm and an outer diameter of 9.9 mm. The peripheral arc zone has an inner diameter of 9.9 mm and an outer diameter of 10.9 mm. The orthokeratology lens 10 has a central thickness of 0.22 mm.

Figure 3B:
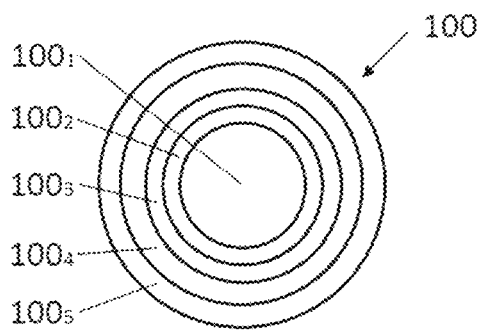
FIG. 3B schematically illustrates the base arc zone of an orthokeratology lens in accordance with a specific embodiment of the present disclosure.

In this embodiment, as shown in FIG. 3B, the base arc zone 100 comprises a central region $100_1$ and four concentric annular regions $100_2$, $100_3$, $100_4$, and $100_5$ surrounding the central region $100_1$. The central region $100_1$ has a diameter of 4 mm. The annular region $100_2$ has an inner diameter of 4 mm and an outer diameter of 4.5 mm. The annular region $100_3$ has an inner diameter of 4.5 mm and an outer diameter of 5 mm. The annular region $100_4$ has an inner diameter of 5 mm and an outer diameter of 5.5 mm. The annular region $100_5$ has an inner diameter of 5.5 mm and an outer diameter of 6.5 mm. The radii of curvature of the regions $100_1$, $100_2$, $100_3$, $100_4$ and $100_5$ gradually decrease outwards from the center. For example, the radius of curvature of the central region $100_1$ may be 7.85 mm, the radius of curvature of the annular region $100_2$ may be 7.76 mm, the radius of curvature of the annular region $100_3$ may be 7.67 mm, the radius of curvature of the annular region $100_4$ may be 7.58 mm, and the radius of curvature of the annular region $100_5$ may be 7.50 mm.

This orthokeratology lens 10 can shape the cornea of a wearer to exhibit a refractive power of 43.0 D, 43.5 D, 44.0 D, 44.5 D and 45.0 D from the center to the edge in sequence, realizing gradually changed refractive power and realizing gradually changed additional refractive power from +0.5 D to +2.0 D.

In the embodiment shown in FIG. 3B, the base arc zone comprises a central zone and four concentric annular regions, with the radii of curvature decreasing outwards from the center to provide five different refractive powers. Moreover, the base arc zone may comprise other numbers of concentric annular regions, thereby providing other numbers of different refractive powers. The diameter of the central region and the radial widths of the annular regions (i.e., half of the difference between the outer diameter and the inner diameter) can be adjusted in accordance with size of the patient's pupil, requirements for near vision clarity, etc.

Myopic peripheral defocusing refers to a condition that the refractive power of the optical system of a human eye is larger at the periphery, forming a focal point falling in front of the retina. Clinical evidences indicate that myopic peripheral defocusing can be used for myopia control of young people. The technical solutions of the present disclosure can bring about technical effects including: when young people wear the orthokeratology lens in accordance with these technical solutions, myopic defocusing can be formed, thereby preventing growth of ocular axis and delaying myopic developing.

In some embodiments of the present disclosure, the central region $100_1$ has a diameter greater than 1 mm, and preferably greater than 2 mm.

In other embodiments of the present disclosure, the two or more regions of the base arc zone are two or more sector-shaped regions, and the two or more sector-shaped regions collectively make up the base arc zone. In other embodiments of the present disclosure, the two or more regions of the base arc zone are two or more sector-shaped regions, and the base arc zone further comprises a smooth transition region between each two adjacent sector-shaped regions, and the two or more sector-shaped regions and the smooth transition regions collectively make up the base arc zone.

For example, in an embodiment, the orthokeratology lens is made of a material that is highly oxygen permeable and rigid, comprising a base arc zone 100', a reversal arc zone, an adaptive arc zone, and a peripheral arc zone. The orthokeratology lens 10' has an overall diameter of 10.6 mm, with the base arc zone 100' having a diameter of 6.2 mm, the reversal arc zone having an inner diameter of 6.2 mm and an outer diameter of 8.0 mm. The adaptive arc zone has an inner diameter of 8.0 mm and an outer diameter of 9.6 mm. The peripheral arc zone has an inner diameter of 9.6 mm and an outer diameter of 10.6 mm. The orthokeratology lens has a central thickness of 0.16 mm.

Figure 4A:
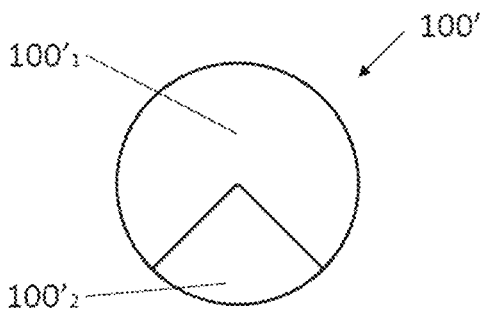
FIG. 4A schematically illustrates the base arc zone of an orthokeratology lens in accordance with a specific embodiment of the present disclosure.

In an embodiment, as shown in FIG. 4A, the two or more regions of the base arc zone 100' of the orthokeratology lens are sector-shaped regions $100'_1$ and $100'_2$, and the sector-shaped regions $100'_1$ and $100'_2$ collectively make up the base arc zone 100'. In this embodiment, the sector-shaped region $100'_1$ has a central angle of 240°, and the sector-shaped region $100'_2$ has a central angle of 120°.

Figure 4B:
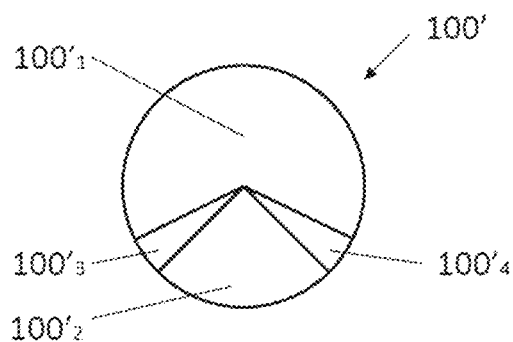
FIG. 4B schematically illustrates the base arc zone of an orthokeratology lens in accordance with a specific embodiment of the present disclosure.

In an embodiment, as shown in FIG. 4B, the two or more regions of the base arc zone 100' of the orthokeratology lens are sector-shaped regions 100'$_1$ and 100'$_2$. The base arc zone 100' further comprises smooth transition regions 100'$_3$ and 100'$_4$ located between the sector-shaped regions 100'$_1$ and 100'$_2$, and the sector-shaped regions 100'$_1$ and 100'$_2$ and the smooth transition regions 100'$_3$ and 100'$_4$ collectively make up the base arc zone 100'. In this embodiment, the sector-shaped region 100'$_1$ has a central angle of 220°, and the sector-shaped region 100'$_2$ has a central angle of 100°. The sector-shaped region 100'$_1$ has a radius of curvature of 9.0 mm and the sector-shaped region 100'$_2$ has a radius of curvature of 9.78 mm. Each of the smooth transition regions 100'$_3$ and 100'$_4$ has a central angles of 20°.

By wearing the orthokeratology lens, after the cornea is shaped, the refractive power of a far vision region is 37.5 D, the refractive power of a near vision region is 34.5 D, and the sector-shaped regions 100'$_1$ and 100'$_2$ of the base arc zone 100' of the orthokeratology lens can provide +3.0 D additional refractive power for the cornea, so that a wearer can simultaneously have double focal points of far vision and near vision, and the optical energy ratio of the two focal points is 2.2:1. Because the two sector-shaped regions are joined by the smooth transition regions, no obvious inter-region mark is left on the cornea after the patient wears the orthokeratology lens.

In the embodiment shown in FIG. 4A and FIG. 4B, the base arc zone comprises two sector-shaped regions. Moreover, the base arc zone may comprise more than two sector-shaped regions, so that more than two focal points are generated. The central angles of the sector-shaped region and the smooth transition region can be adjusted as desired.

In other embodiments of the present disclosure, two or more regions of the base arc zone may be irregularly shaped.

Figure 5A:
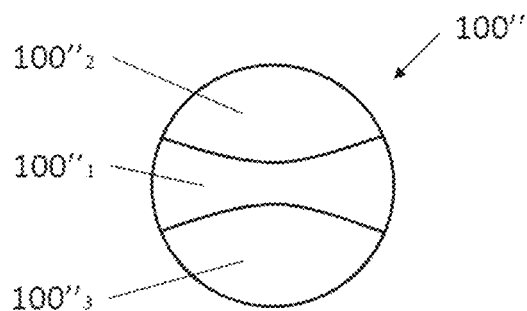
FIG. 5A schematically illustrates the base arc zone of an orthokeratology lens in accordance with a specific embodiment of the present disclosure.

For example, in an embodiment, as shown in FIG. 5A, two or more regions of the base arc zone 100" are a first region 100"$_1$ located in the middle and a second region 100"$_2$ and a third region 100"$_3$ located on either side of the first region 100"$_1$, and the first region 100"$_1$, the second region 100"$_2$ and the third region 100"$_3$ collectively make up the base arc zone 100". In another embodiment, as shown in FIG. 5B, the two or more regions of the base arc zone 100" are a first region 100"$_1$ located in the middle and a second region 100"$_2$ and a third region 100"$_3$ located on either side of the first region 100"$_1$, the base arc zone 100" may further comprise a first smooth transition region 100"$_4$ located between the first region 100"$_1$ and the second region 100"$_2$ and a second smooth transition region 100"$_5$ located between the first region 100"$_1$ and the third region 100"$_3$, and the first region 100"$_1$, the second region 100"$_2$, the third region 100"$_3$, the first smooth transition region 100"$_4$ and the second smooth transition region 100"$_5$ collectively make up the base arc zone 100".

Figure 5B:
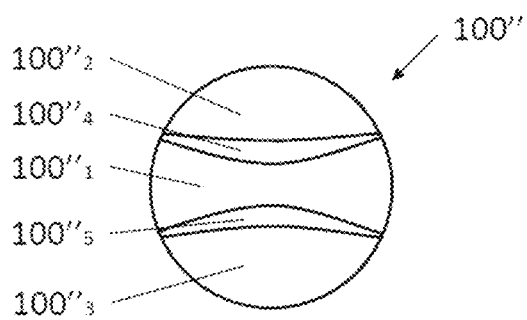
FIG. 5B schematically illustrates the base arc zone of an orthokeratology lens in accordance with a specific embodiment of the present disclosure.

In the embodiment shown in FIG. 5A and FIG. 5B, the first region 100"$_1$ has a radius of curvature of 7.30 mm, the second region 100"$_2$ has a radius of curvature of is 7.00 mm, and the third region 100"$_3$ has a radius of curvature of 7.63 mm. After the cornea is shaped, the first region 100"$_1$ generates a refractive power of 46.2 D, the second region 100"$_2$ generates a refractive power of 48.2 D, and the third region 100"$_3$ generates a refractive power of 44.2 D, so that a full-range vision of far vision, +2.0 D mid-range vision and +4.0 D near vision can be realized for the human eye.

In the embodiment shown in FIG. 5A and FIG. 5B, the two or more regions of the base arc zone are three irregularly shaped regions. Moreover, the two or more regions of the base arc zone may be other numbers of irregularly shaped regions, thereby providing other numbers of focal points.

Figure 5C:
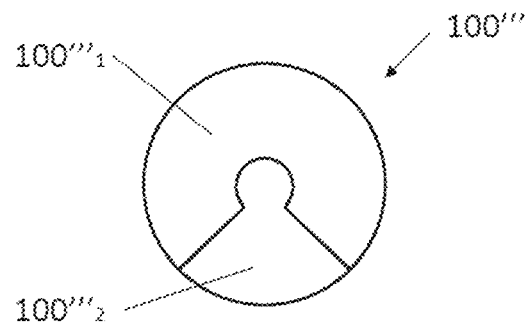
FIG. 5C schematically illustrates the base arc zone of an orthokeratology lens in accordance with a particular embodiment of the present disclosure.
Figure 5D:
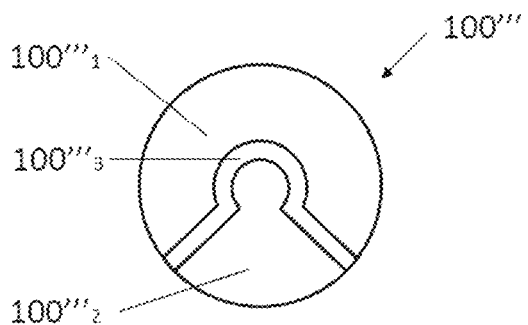
FIG. 5D schematically illustrates the base arc zone of an orthokeratology lens in accordance with a specific embodiment of the present disclosure.

For example, in an embodiment, as shown in FIG. 5C, the two or more regions of the base arc zone 100''' are a first region 100'''$_1$ and a second region 100'''$_2$, the first region 100'''$_1$ is a part of a circular ring, the second region 100'''$_2$ has a completely circular portion in its center, and the first region 100'''$_1$ and the second region 100'''$_2$ collectively make up the base arc zone 100'''. In this embodiment, the first region 100'''$_1$ has a radius of curvature of 7.50 mm and the second region 100'''$_2$ has a radius of curvature of 7.85 mm. After the cornea is shaped, the first region 100'''$_1$ generates a refractive power of 45.0 D, and the second region 100'''$_2$ generates a refractive power of 43.0 D, so that a vision of far vision and +2.0 D near vision can be realized for the human eye. The first region 100'''$_1$ has a central angle of 200°, the second region 100'''$_2$ has a central angle of 160°, and the second region 100'''$_2$ has a complete circular portion in its center with a diameter of 2.0 mm. In another embodiment, as shown in FIG. 5D, the two or more regions of the base arc zone 100''' are a first region 100'''$_1$ and a second region 100'''$_2$, the first region 100'''$_1$ is a part of a circular ring, the second region 100'''$_2$ has a completely circular portion in its center, the base arc zone 100''' further comprises a smooth transition region 100'''$_3$ located between the first region 100'''$_1$ and the second region 100'''$_2$, and the first region 100'''$_1$, the second region 100'''$_2$ and the smooth transition region 100'''$_3$ collectively make up the base arc zone 100'''. In this embodiment, the first region 100'''$_1$ has a radius of curvature of 8.44 mm, the second region 100'''$_2$ has a radius of curvature of 7.85 mm, and the third region 100'''$_3$ is a smooth transition portion having a width of 0.1 mm and a radius of curvature between the radii of curvature of the first region and the second region. After the cornea is shaped, the first region 100'''$_1$ generates a refractive power of 40.0 D, and the second region 100'''$_2$ generates a refractive power of 43.0 D, so that a vision of far vision and +3.0 D near vision can be realized for the human eye. The first region 100'''$_1$ has a central angle of 220°, the second region 100'''$_2$ has a central angle of 120°, and the second region 100'''$_2$ has a complete circular portion in its center with a diameter of 1.8 mm.

In the embodiment shown in FIG. 5C and FIG. 5D, the two or more regions of the base arc zone are two irregularly shaped regions. Moreover, the two or more regions of the base arc zone may be other numbers of irregularly shaped regions, thereby providing other numbers of focal points.

In some embodiments, the cornea has a refractive power K of 38.0 D to 47.0 D, the amount of ametropia correction is −6.0 D to 1.0 D, and the maximum radius of curvature $R_1$ of the base arc zone is calculated to be 6.0 mm to 10.5 mm in accordance with equation (2). In combination with the above range, the minimum radius of curvature $R_2$ of the base arc zone can be calculated from equation (5). Table 1 shows data in accordance with some embodiments of the present disclosure, wherein the refractive index n of the cornea is 1.3375.

TABLE 1

The maximum radius of curvature $R_1$ of the base arc zone and the minimum radius of curvature $R_2$ corresponding to different amounts of presbyopia correction $\Delta T$

| $\Delta T$ | 0.50 | 0.75 | 1.00 | 1.50 | 2.00 | 2.50 | 3.00 | 3.50 | 4.00 | 4.50 | 5.00 |
|---|---|---|---|---|---|---|---|---|---|---|---|
| $R_1$ | 6.00 | 6.00 | 6.00 | 6.00 | 6.00 | 6.00 | 6.00 | 6.00 | 6.00 | 6.00 | 6.00 |
| $R_2$ | 5.95 | 5.92 | 5.90 | 5.84 | 5.79 | 5.74 | 5.70 | 5.65 | 5.60 | 5.56 | 5.51 |
| $R_1$ | 7.00 | 7.00 | 7.00 | 7.00 | 7.00 | 7.00 | 7.00 | 7.00 | 7.00 | 7.00 | 7.00 |
| $R_2$ | 6.93 | 6.89 | 6.86 | 6.79 | 6.72 | 6.65 | 6.59 | 6.53 | 6.46 | 6.40 | 6.34 |
| $R_1$ | 7.50 | 7.50 | 7.50 | 7.50 | 7.50 | 7.50 | 7.50 | 7.50 | 7.50 | 7.50 | 7.50 |
| $R_2$ | 7.42 | 7.38 | 7.34 | 7.26 | 7.18 | 7.11 | 7.03 | 6.96 | 6.89 | 6.82 | 6.75 |
| $R_1$ | 8.50 | 8.50 | 8.50 | 8.50 | 8.50 | 8.50 | 8.50 | 8.50 | 8.50 | 8.50 | 8.50 |
| $R_2$ | 8.39 | 8.34 | 8.29 | 8.19 | 8.09 | 8.00 | 7.90 | 7.81 | 7.72 | 7.63 | 7.55 |
| $R_1$ | 9.00 | 9.00 | 9.00 | 9.00 | 9.00 | 9.00 | 9.00 | 9.00 | 9.00 | 9.00 | 9.00 |
| $R_2$ | 8.88 | 8.82 | 8.77 | 8.65 | 8.54 | 8.44 | 8.33 | 8.23 | 8.13 | 8.04 | 7.94 |
| $R_1$ | 9.50 | 9.50 | 9.50 | 9.50 | 9.50 | 9.50 | 9.50 | 9.50 | 9.50 | 9.50 | 9.50 |
| $R_2$ | 9.37 | 9.30 | 9.24 | 9.12 | 8.99 | 8.88 | 8.76 | 8.65 | 8.54 | 8.43 | 8.33 |
| $R_1$ | 9.93 | 9.93 | 9.93 | 9.93 | 9.93 | 9.93 | 9.93 | 9.93 | 9.93 | 9.93 | 9.93 |
| $R_2$ | 9.79 | 9.72 | 9.65 | 9.51 | 9.38 | 9.25 | 9.12 | 9.00 | 8.88 | 8.77 | 8.66 |
| $R_1$ | 10.00 | 10.00 | 10.00 | 10.00 | 10.00 | 10.00 | 10.00 | 10.00 | 10.00 | 10.00 | 10.00 |
| $R_2$ | 9.85 | 9.78 | 9.71 | 9.57 | 9.44 | 9.31 | 9.18 | 9.06 | 8.94 | 8.82 | 8.71 |
| $R_1$ | 10.50 | 10.50 | 10.50 | 10.50 | 10.50 | 10.50 | 10.50 | 10.50 | 10.50 | 10.50 | 10.50 |
| $R_2$ | 10.34 | 10.26 | 10.18 | 10.03 | 9.88 | 9.74 | 9.60 | 9.47 | 9.34 | 9.21 | 9.09 |

In some embodiments of the present disclosure, the orthokeratology lens provides an amount of presbyopia correction $\Delta T$ of +0.5 D to +5.0 D, preferably +0.75 D to +3.5 D, and more preferably +1.0 D to +3.0 D for a human eye.

In some embodiments of the present disclosure, the base arc zone of the orthokeratology lens has a maximum radius of curvature of 6.0 mm to 10.5 mm, and preferably 7.0 mm to 10.0 mm.

In some embodiments of the present disclosure, the base arc zone of the orthokeratology lens has a minimum radius of curvature of 5.51 mm to 10.34 mm, preferably 5.65 mm to 9.85 mm, and more preferably 6.53 mm to 9.71 mm.

In some embodiments of the present disclosure, the base arc zone of the orthokeratology lens has a diameter of 4.5 mm to 7.0 mm, preferably 5.0 mm to 6.8 mm, and more preferably 5.2 mm to 6.5 mm.

When n is 1.3375, equation (1) is expressed as:

$$K = \frac{337.5}{R} \qquad (10)$$

When the patient has ametropia, the radius of curvature of the anterior surface of the cornea of the human eye, namely R in the equations (1) and (10), is adjusted by the base arc zone BC of the orthokeratology lens, so that correction of the ametropia of the human eye can be realized. In some embodiments of the present disclosure, the base arc zone BC is circular as seen in a direction parallel to the optical axis. However, in other embodiments of the present disclosure, the base arc zone BC may have other shapes, such as elliptical, oval, etc., as seen in a direction parallel to the optical axis.

When people wear the orthokeratology lens and sleep with eyes closed, eyelids apply pressing force to the orthokeratology lens and the cornea. Since the human eye has an approximately spherical shape, the pressing force gradually decreases from the highest point in the center of the cornea to the edge. This characteristic of the pressing force is such that after wearing the orthokeratology lens, no matter how the central region of the orthokeratology lens is designed, the central region of the cornea cannot be raised, and must be flattened. Therefore, the region for presbyopia correction cannot be located in the central region of the orthokeratology lens.

On the other hand, in order for the human eye to receive an image of the presbyopia correction region of the cornea under normal pupil conditions, the presbyopia correction region must be sufficiently close to the center.

Moreover, the presbyopia correction region of the cornea has a smaller radius of curvature than other regions and is "raised" in that pressure from other regions is necessary to cause cornea cells to migrate toward the presbyopia correction region.

In another aspect of the present disclosure, the present disclosure innovatively provides that the base arc zone of the orthokeratology lens has at least two different radii of curvature, so that the human eye, after wearing the orthokeratology lens, generates a gradual refractive power change in the optical zone of the cornea, thereby extending the depth of field of the patient and correcting ametropia and presbyopia simultaneously. More particularly, the orthokeratology lens of the present disclosure comprises an inner surface facing a cornea of a human eye when the orthokeratology lens is worn and an outer surface opposite the inner surface. The inner surface comprises a centrally located base arc zone. The base arc zone comprises a centrally located circular first region, a circular ring shaped second region surrounding the first region and a third region surrounding the second region, and the surface shapes of the first region, the second region and the third region can be spherical surfaces. A radius of curvature of the second region is smaller than a radius of curvature of the first region, and the radius of curvature of the second region is smaller than a radius of curvature of the third region.

The difference of the radii of curvature of the first region and the second region enables the orthokeratology lens to generate different shaping effects to the cornea, and the difference of the radii of curvature of the two regions is a design value of the amount of presbyopia correction of the orthokeratology lens. In the orthokeratology lens of the present disclosure, preferably, the design value of the amount of presbyopia correction should be 0.5 D to 6.0 D, that is, the radii of curvature of the first region and the second region satisfy the following relationship:

$$0.5 \leq 337.5 * \left(\frac{1}{R_B} - \frac{1}{R_A}\right) \leq 6.0$$

where $R_A$ and $R_B$ are radii of curvature in millimeters (mm) for the first region and the second region, respectively, and $$337.5 * \left(\frac{1}{R_B} - \frac{1}{R_A}\right)$$

represents the amount of presbyopia correction of the second region of the orthokeratology lens relative to the first region.

Figure 6:
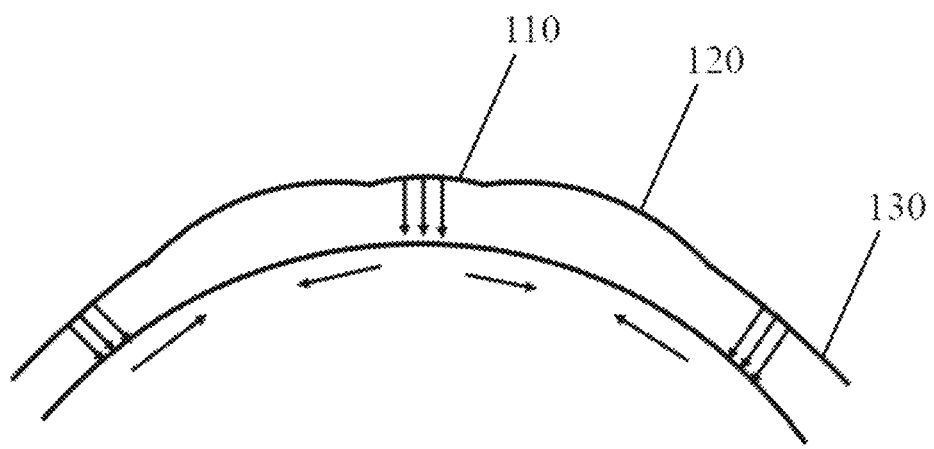
FIG. 6 schematically shows "seesaw" three-region structure of the base arc zone of the orthokeratology lens of the present disclosure and migration of cells after the cornea is stressed.

In the orthokeratology lens of the present disclosure, the three regions of the base arc zone are flat-raised-flat and formed like a seesaw to guide the cornea cells toward the second region, as indicated by arrows in FIG. 6. The first region 110 of the base arc zone has a relatively flat shape (i.e., a relatively large radius of curvature), so that the cornea is pressed at the center to compress the cornea cells toward both sides, which conforms to the force law when the orthokeratology lens is worn and the eyes are closed, and is the force-bearing fulcrum of the orthokeratology lens. The third region 130 of the base arc zone also has a relatively flat shape (i.e., a relatively large radius of curvature), compressing the cornea cells toward both sides. The second region 120 of the base arc zone has a relatively steep shape (i.e., a relatively small radius of curvature) that is spaced from the cornea, creating an opposite attractive force that causes the cells compressed at the first region 110 and the third region 130 to move toward the second region 120, causing the cornea surface at the second region 120 to be steeper or raised, thereby successfully creating a "presbyopia correction region" of the cornea. The greater the pressure on either side of the second region 120, the easier it is for the cornea surface at the second region 120 to raise. The smaller the radial width of the second region 120, the easier it is for the cornea surface at the second region 120 to raise.

Figure 7:
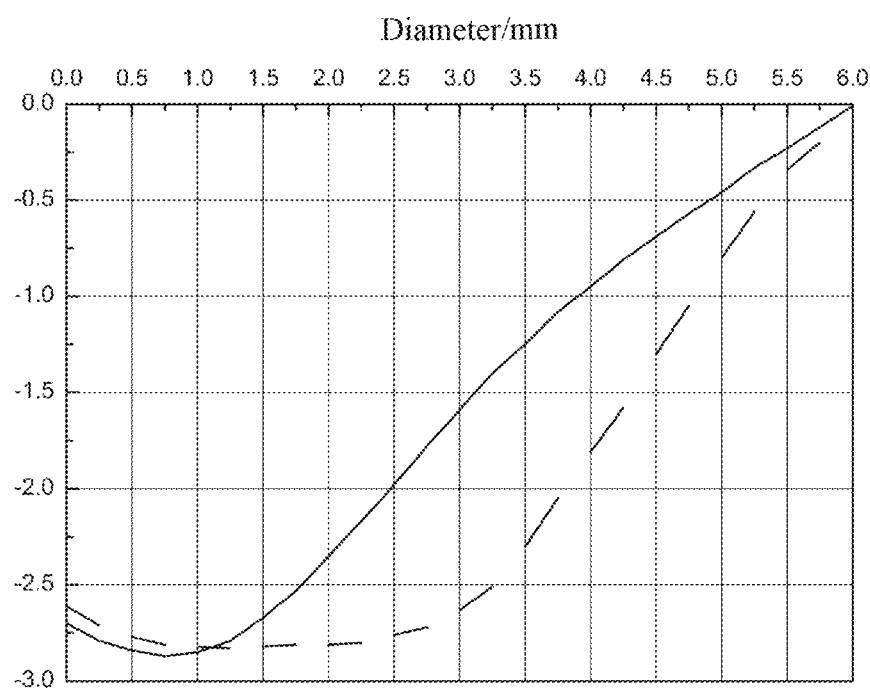
FIG. 7 schematically shows change in refractive power of the cornea before and after wearing the orthokeratology lens of the present disclosure, wherein the abscissa is the diameter of the cornea in millimeters, and the ordinate is the change in refractive power of the cornea before and after wearing, i.e., the refractive power of the cornea at that point after wearing minus the refractive power of the cornea at that point before wearing, in D (diopter), wherein the solid line shows the case where the diameter of the first region of the base arc zone is 1 mm, and the dotted line shows the case where the diameter of the first region of the base arc zone is 2 mm.

When the cornea is shaped by pressing, the radius of curvature of the cornea surface at each region is not abruptly changed but gradually changed due to continuity of the elastic surface of the cell, so that the first region 110 of the base arc zone is preferably not too large, so that the position of the presbyopia correction region of the cornea corresponding to the second region 120 of the base arc zone is not beyond the range of the pupil capable of receiving the image. Thus, in the orthokeratology lens of the present disclosure, the first region of the base arc zone has a diameter of 0.50 mm to 1.75 mm, preferably 0.50 mm to 1.5 mm, and more preferably 1.0 mm. The solid line in FIG. 7 shows change in refractive power of the cornea after wearing the orthokeratology lens of the present disclosure, wherein the first region of the base arc zone has a diameter of 1 mm. It can be seen that the first region acts to flatten the cornea to correct myopia in the human eye, producing a refractive power change of about −2.5 D. The second region is a presbyopia shaping region that shapes the cornea such that the change in refractive power at the second region is smaller than the change in refractive power at the first region, thereby allowing the cornea to form a presbyopia correction region at the second region. Theoretically, the location of the presbyopia correction region of the cornea should correspond to the location of the second region of the base arc zone. However, since the radius of curvature of the cornea surface is not abruptly changed but gradually changed, the presbyopia correction region of the cornea occurs at a greater diameter than the second region, i.e., at a diameter of about 1.5 mm or so, and the refractive power is gradually changed outwards from the center. The dotted line in FIG. 7 shows change in refractive power of the cornea after wearing the orthokeratology lens of the present disclosure, wherein the first region of the base arc zone has a diameter of 2 mm. It can be seen that if the diameter of the first region exceeds 1.75 mm, the presbyopia correction region of the cornea, i.e. the region of reduced refractive power change, will extends to about 3 mm in diameter, and will not allow the human eye to simultaneously have clear near vision and far vision.

The principle of the present disclosure is to reduce requirements of accommodation for the human eye lens by inducing changes in optical properties of the cornea through changes in the shape of the cornea. By this mechanism, the orthokeratology lens of the present disclosure can be used for relieving visual fatigue. Moreover, after the cornea is shaped by the orthokeratology lens of the present disclosure, the refractive power of the cornea at the second region is larger than that at the first region, the human eye can therefore form myopic peripheral defocusing, so the orthokeratology lens can also be used to myopia control of young people.

Embodiment 1

The cornea of wearer 1 has a refractive power K of 42.00 D, a radius of curvature of 8.04 mm, and a myopia of −2.50 D. The parameters of the orthokeratology lens customized for wearer 1 are shown in Table 2.

TABLE 2

| Parameters of the orthokeratology lens customized for wearer 1 | |
|---|---|
| Diameter of base arc zone | 10.6 mm |
| Diameter of the first region | 1.0 mm |
| Radial width of the second region | 1.0 mm |
| Radial width of the third region | 1.6 mm |
| Radius of curvature of the first region | 8.71 mm |
| Radius of curvature of the second region | 8.28 mm |
| Radius of curvature of the third region | 8.71 mm |
| Radius of curvature of outer surface of base arc zone | 8.65 mm |

With the parameters of the orthokeratology lens shown in Table 2, the first region has a radius of curvature of 8.71 mm which is greater than the radius of curvature of the cornea of wearer 1, so the surface shape of the first region is flatter relative to the cornea of wearer 1, serving to flatten the cornea and to correct myopia. The second region has a radius of curvature of 8.28 mm which is smaller than the radius of curvature of the first region, so the second region has a steeper surface shape than the first region, serving to relax the pressure on the cornea and acting as a presbyopia shaping region. The third region has a radius of curvature of 8.71 mm which is the same as the radius of curvature of the first region, serving to flatten the cornea and to migrate cornea cells to both sides. The reversal arc zone, the adaptive arc zone and the peripheral arc zone may be of conventional configurations. For example, the reversal arc zone has a radial width of 0.8 mm and a radius of curvature of 7.60 mm; the adaptive arc zone has a radial width of 0.9 mm and a radius of curvature of 8.04 mm, and the peripheral arc zone has a radial width of 0.5 mm and a radius of curvature of 10.26 mm.

With the parameters of the orthokeratology lens shown in Table 2, the pressing force applied to the cornea from the center to the outside exhibits a high-low-high distribution, which causes the cornea cells to move and deform from the first region and the third region to the second region, so that the cornea is shaped into a shape which is highly flattened at the first region, slightly flattened at the second region, and highly flattened at the third region.

Figure 8:
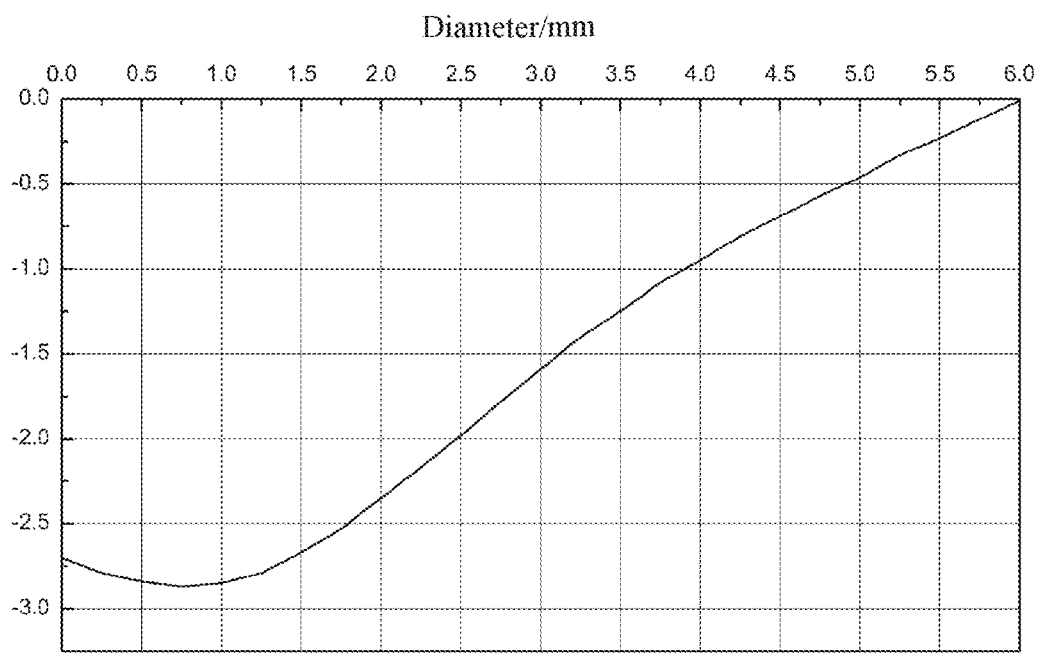
FIG. 8 schematically shows change in refractive power of the cornea before and after wearer 1 wears the orthokeratology lens in embodiment 1 of the present disclosure, where the abscissa is the diameter of the cornea in millimeters and the ordinate is the change in refractive power of the cornea before and after wearing, i.e., the refractive power of the cornea at that point after wearing minus the refractive power of the cornea at that point before wearing, in D (diopter).

The migration and deformation of the cornea cells is a gradual process. FIG. 8 shows change in refractive power of the cornea before and after the orthokeratology lens of embodiment 1 is worn. As can be seen from the results after wearing, the change in refractive power within 1 mm of the central region of the cornea is about −2.5 D, and the cornea of wearer 1 achieves sufficient change in refractive power to enable myopia correction. The first region of the base arc zone of the orthokeratology lens has a diameter of 1 mm, but a transition region of about 0.5 mm is needed for the cornea to change the radius of curvature from the radius of curvature of the first region to the radius of curvature of the second region, the amount of refractive power change is reduced from the cornea diameter of about 1.5 mm, the amount of refractive power change is reduced significantly at the cornea diameter of about 2.0 mm, and the amount of refractive power change is reduced to −1.5 D at the cornea diameter of about 3.0 mm, so that human eye can form a plurality of focal points within a normal pupil diameter, the depth of field is expanded, and presbyopia is corrected.

Figure 9A:
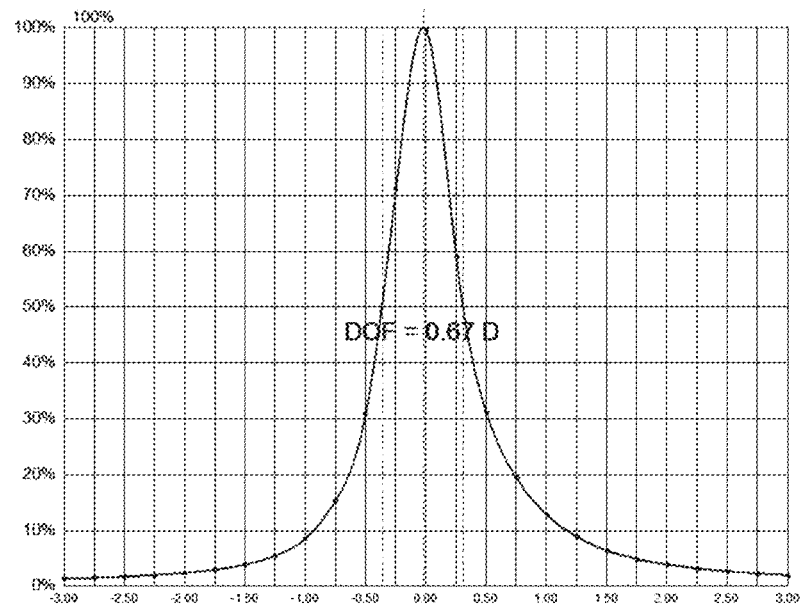
FIG. 9A shows the depth of field of wearer 1 before wearing orthokeratology lens in embodiment 1 of the present disclosure, as measured using the depth of field measurement function of the iTrace visual function analyzer, wherein the measured pupil size is 3.0 mm, wherein the abscissa is refractive power in D (diopter), representing addition of different refractive powers in front of and behind emmetropia (refractive power of 0 D) of the human eye, and the ordinate is the normalized contrast sensitivity, with the depth of field (DOF) of the human eye being difference between additional refractive powers in front of and behind emmetropia when the contrast sensitivity is decreased to 50%.
Figure 9B:
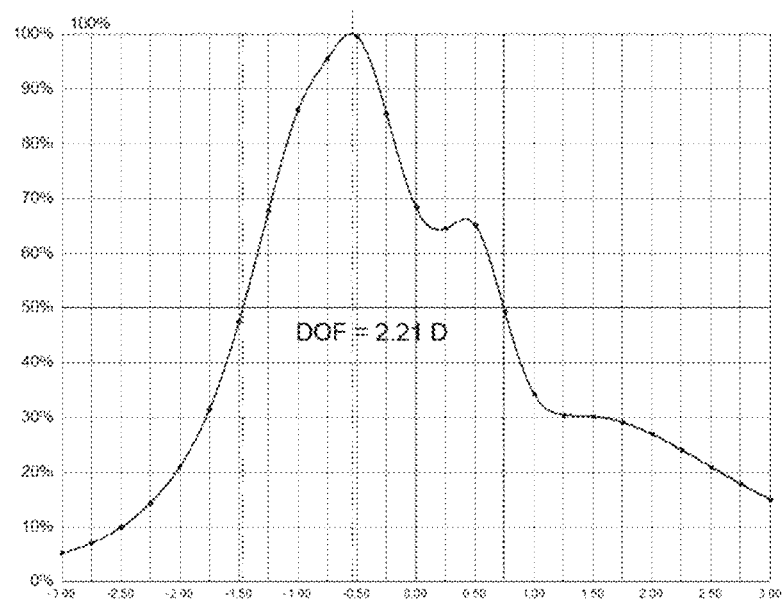
FIG. 9B shows the depth of field of wearer 1 after wearing orthokeratology lens in embodiment 1 of the present disclosure, as measured using the depth of field measurement function of the iTrace visual function analyzer, wherein the measured pupil size is 3.0 mm, wherein the abscissa is refractive power in D (diopter), representing addition of different refractive powers in front of and behind emmetropia (refractive power of 0 D) of the human eye, and the ordinate is the normalized contrast sensitivity, with the depth of field (DOF) of the human eye being difference between additional refractive powers in front of and behind emmetropia when the contrast sensitivity is decreased to 50%.

Under the action of the orthokeratology lens of embodiment 1, wearer 1 is provided with a change in refractive power of about −1.5 D within the 3.0 mm pupil. FIG. 9A and FIG. 9B respectively show the depth of field of wearer 1 before and after wearing the orthokeratology lens of embodiment 1 measured by depth of field measurement function of iTrace visual function analyzer. It can be seen that after wearing the orthokeratology lens of embodiment 1, the depth of field of wearer 1 is greatly improved, so as to obtain the presbyopia correction effect.

Embodiment 2

The cornea of wearer 1 has a refractive power K of 44.75 D, a radius of curvature of 7.54 mm, and no myopia. The parameters of the orthokeratology lens customized for wearer 2 are shown in Table 3.

TABLE 3

Parameters of orthokeratology lens customized for wearer 2

| | |
|---|---|
| Diameter of base arc zone | 10.6 mm |
| Diameter of the first region | 1.0 mm |
| Radial width of the second region | 1.0 mm |
| Radial width of the third region | 1.6 mm |
| Radius of curvature of the first region | 7.54 mm |
| Radius of curvature of the second region | 6.78 mm |
| Radius of curvature of the third region | 7.54 mm |
| Radius of curvature of outer surface of base arc zone | 7.61 mm |

With the parameters of the orthokeratology lens shown in Table 3, the first region has a radius of curvature of 7.54 mm which is the same as the radius of curvature of the cornea of wearer 2, serving for normal far vision. The second region has a radius of curvature of 6.78 mm which is smaller than the radius of curvature of the first region, so the second region has a steeper surface shape than the first region, acting as a presbyopic shaping region, serving to apply a negative pressure on the cornea and attract cornea cells in the peripheral region to migrate to this region. The third region has a radius of curvature of 7.54 mm which is the same as the radius of curvature of the first region, serving to migrate cornea cells to both sides. The reversal arc zone, the adaptive arc zone and the peripheral arc zone may be of conventional configurations. For example, the reversal arc zone has a radial width of 0.8 mm and a radius of curvature of 8.12 mm; the adaptive arc zone has a radial width of 0.9 mm and a radius of curvature of 7.54 mm, and the peripheral arc zone has a radial width of 0.5 mm and a radius of curvature of 9.39 mm.

With the parameters of the orthokeratology lens shown in Table 3, the pressing force applied to the cornea from the center to the outside exhibits a low-lower-low distribution, which causes the cornea cells to move and deform from the first region and the third region to the second region, so that the cornea is shaped into a shape which is mildly flattened at the first region, raised at the second region, and mildly flattened at the third region. Wearer 2 has no myopia. Hence, being mildly flattened at the first region causes wearer 2 to drift towards far vision in the first region, and because the cornea is raised at the second region, a higher refractive power than the human eye itself is provided. There is a transition region from the first region to the second region which provides a refractive power of emmetropia for the human eye.

Figure 10:
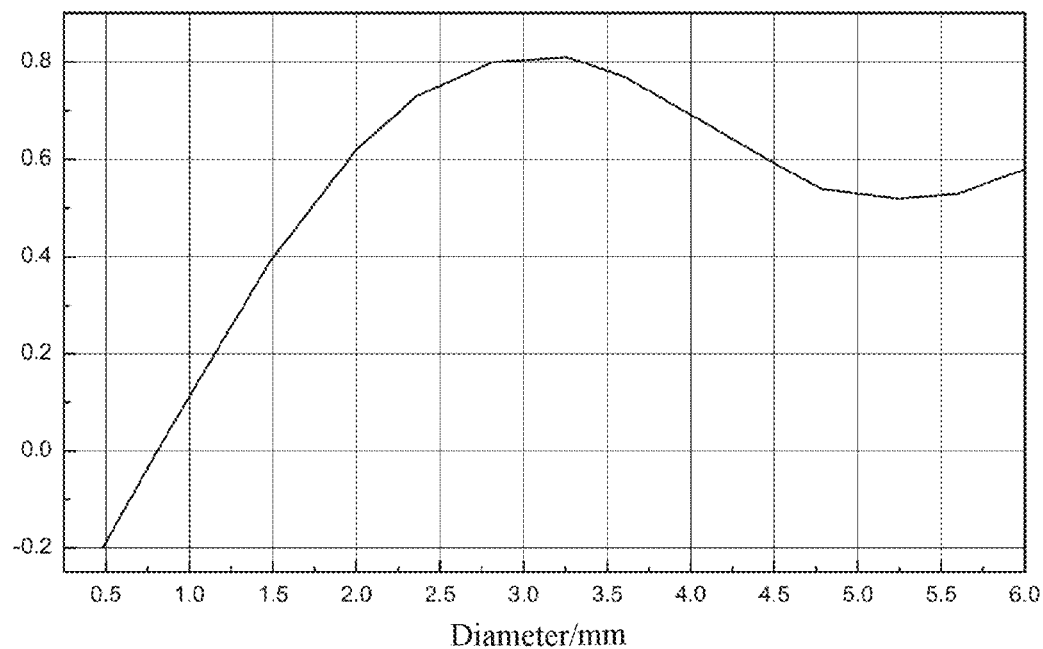
FIG. 10 schematically shows the change in refractive power of the cornea before and after wearer 2 wears the orthokeratology lens in embodiment 2 of the present disclosure, where the abscissa is the diameter of the cornea in millimeters and the ordinate is the change in refractive power of the cornea before and after wearing, i.e., the refractive power of the cornea at that point after wearing minus the refractive power of the cornea at that point before wearing, in D (diopter).

The migration and deformation of the cornea cells is a gradual process. FIG. 10 shows change in refractive power of the cornea before and after the orthokeratology lens of embodiment 2 is worn. As can be seen from the results after wearing, the cornea of wearer 2 has a refractive power change of ±0.2 D within a diameter of 1 mm, indicating that wearer 2 maintains an emmetropic condition in the central region of the cornea, substantially without altering the original refractive condition of wearer 2. Beyond 1 mm, the refractive power of the cornea rapidly increases, with the highest refractive power change at 3.0 mm.

Figure 11A:
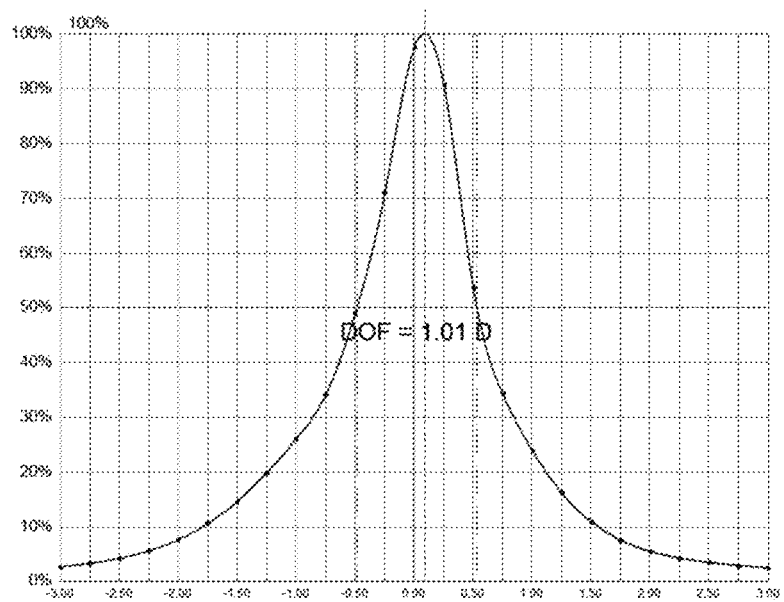
FIG. 11A shows the depth of field of wearer 2 before wearing orthokeratology lens in embodiment 2 of the present disclosure, as measured using the depth of field measurement function of the iTrace visual function analyzer, wherein the measured pupil size is 3.0 mm, wherein the abscissa is refractive power in D (diopter), representing addition of different refractive powers in front of and behind emmetropia (refractive power of 0 D) of the human eye, and the ordinate is the normalized contrast sensitivity, with the depth of field (DOF) of the human eye being difference between additional refractive powers in front of and behind emmetropia when the contrast sensitivity is decreased to 50%.
Figure 11B:
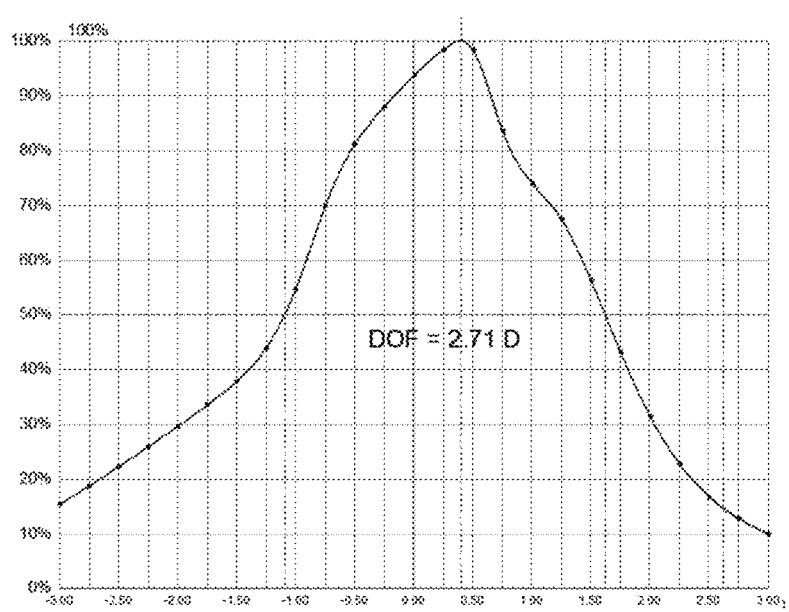
FIG. 11B shows the depth of field of wearer 2 after wearing orthokeratology lens in embodiment 2 of the present disclosure, as measured using the depth of field measurement function of the iTrace visual function analyzer, wherein the measured pupil size is 3.0 mm, wherein the abscissa is refractive power in D (diopter), representing addition of different refractive powers in front of and behind emmetropia (refractive power of 0 D) of the human eye, and the ordinate is the normalized contrast sensitivity, with the depth of field (DOF) of the human eye being difference between additional refractive powers in front of and behind emmetropia when the contrast sensitivity is decreased to 50%.

Under the action of the orthokeratology lens of embodiment 2, the cornea of wearer 2 is raised at the second region, resulting in a presbyopia correction effect. FIGS. 11a and 11b respectively show the depth of field of wearer 2 before and after wearing the orthokeratology lens of embodiment 2 measured by depth of field measurement function of iTrace visual function analyzer. It can be seen that after wearing the orthokeratology lens of embodiment 2, the depth of field of wearer 2 is improved.

Embodiments 3 to 9

Table 4 illustrates some embodiments of orthokeratology lenses in accordance with the present disclosure. For the orthokeratology lens of the present disclosure, the base arc zone may have a diameter of 4.5 mm to 8.0 mm, preferably 5.0 mm to 7.0 mm, and more preferably 5.2 mm to 6.5 mm. Typically, the cornea of the wearer has a refractive power K of 40.15 D to 56.25 D and an amount of ametropia $K_A$ of 0 to −8.0 D. More commonly, the refractive power of the cornea K is 39.75 D to 46.22 D and the amount of ametropia $K_A$ is 0 to −6.0 D. The relation between the radius of curvature of the first region $R_A$, the refractive power of the cornea K and the amount of ametropia is as follows: $R_A=337.5/(K+K_A)$.

Accordingly, the radius of curvature of the first and third regions may be 6.0 mm to 10.5 mm, and preferably 7.0 mm to 10.0 mm. The radius of curvature of the second region may be 5.42 mm to 10.34 mm, and preferably 6.22 mm to 9.85 mm. The diameter of the first region may be 0.50 mm to 1.75 mm, preferably 0.50 mm to 1.5 mm, and more preferably 1.0 mm. The radial width of the second region may be 0.75 mm to 1.5 mm, preferably 1.0 mm to 1.25 mm, and more preferably 1.0 mm. The radial width of the third region may be 0.75 mm to 3.0 mm, preferably 1.0 mm to 2.0 mm, and more preferably 1.0 mm to 1.75 mm.

TABLE 4

Parameter of orthokeratology lenses customized for the wearer (in millimeters)

| | Embodiment 3 | Embodiment 4 | Embodiment 5 | Embodiment 6 | Embodiment 7 | Embodiment 8 | Embodiment 9 |
|---|---|---|---|---|---|---|---|
| Diameter of base arc zone | 8.0 | 7.75 | 7.0 | 6.5 | 5.2 | 5 | 4.5 |
| Diameter of the first region | 0.5 | 1.75 | 1 | 1.5 | 1 | 1 | 1.5 |
| Radial width of the second region | 0.75 | 1.25 | 1 | 1.5 | 1 | 1 | 0.75 |
| Radial width of the third region | 3.0 | 1.75 | 2 | 1 | 1.1 | 1 | 0.75 |
| Radial width of reversal arc zone | 0.4 | 1.0 | 1.0 | 0.8 | 0.9 | 1.0 | 1.0 |
| Radial width of adaptive arc zone | 1.0 | 0.4 | 0.7 | 0.9 | 1.0 | 1.1 | 1.25 |
| Radial width of peripheral arc zone | 0.5 | 0.5 | 0.5 | 0.5 | 0.5 | 0.5 | 0.5 |
| Radius of curvature of the first region | 6.00 | 10.50 | 7.00 | 8.60 | 8.18 | 8.39 | 10.0 |
| Radius of curvature of the second region | 5.42 | 10.34 | 6.22 | 7.99 | 7.80 | 7.63 | 9.85 |
| Radius of curvature of the third region | 6.00 | 10.50 | 7.00 | 8.60 | 8.18 | 8.39 | 10.00 |
| Radius of curvature of reversal arc zone | 6.20 | 7.19 | 6.98 | 7.54 | 7.19 | 6.95 | 7.50 |
| Radius of curvature of adaptive arc zone | 5.79 | 8.41 | 6.72 | 7.85 | 7.50 | 7.34 | 8.33 |
| Radius of curvature of peripheral arc zone | 6.24 | 10.53 | 7.79 | 9.81 | 9.56 | 9.19 | 11.10 |
| Radius of curvature of outer surface of base arc zone | 6.00 | 10.38 | 6.98 | 8.54 | 8.13 | 8.33 | 9.90 |

While the present disclosure has been described with reference to exemplary embodiment(s), those skilled in the art will appreciate that the present disclosure is not limited to the precise construction and components described herein and that various modifications, changes, and variations may be apparent from the foregoing descriptions without departing from the spirit and scope of the present disclosure as defined in the appended claims. The present disclosure is not limited by the illustrated ordering of steps, as some steps may occur in different orders and/or concurrently with other steps. Therefore, it is intended that the present disclosure not be limited to the particular embodiment(s) disclosed, but that the present disclosure will include all embodiments falling within the scope of the appended claims.

The invention claimed is:

1. An orthokeratology lens comprising an inner surface facing a cornea of a human eye when the orthokeratology lens is worn and an outer surface opposite the inner surface, the inner surface comprising a centrally located base arc zone, wherein the base arc zone is configured for pressing and shaping an anterior surface of the cornea to have a shape that conforms to the base arc zone, wherein the base arc zone comprises two or more regions, at least two of the two or more regions having different radii of curvature, wherein ΔT calculated from the following equation is from +0.5 D to +5.0 D, preferably from +0.75 D to +3.5 D, and more preferably from +1.0 D to +3.0 D:

$$\Delta T = 1000 * (n-1)\left(\frac{1}{R_2} - \frac{1}{R_1}\right)$$

where $R_1$ is the maximum radius of curvature of the base arc zone in millimeters, $R_2$ is the minimum radius of curvature of the base arc zone in millimeters, n is the refractive index of the cornea with a value of 1.3375.

2. The orthokeratology lens of claim 1, wherein the two or more regions of the base arc zone comprise a centrally located circular central region and one or more concentric annular regions surrounding the central region.

3. The orthokeratology lens of claim 2, wherein the radii of curvature of the two or more regions of the base arc zone alternate in a radial direction.

4. The orthokeratology lens of claim 2, wherein the radii of curvature of the two or more regions of the base arc zone gradually decrease outwards from the center.

5. The orthokeratology lens of claim 2, wherein the central region has a diameter greater than 1 mm, and preferably greater than 2 mm.

6. The orthokeratology lens of claim 1, wherein the two or more regions of the base arc zone are two or more sector-shaped regions, and the two or more sector-shaped regions collectively make up the base arc zone.

7. The orthokeratology lens of claim 1, wherein the two or more regions of the base arc zone are two or more sector-shaped regions, the base arc zone further comprises a smooth transition region between each two adjacent sector-shaped regions, and wherein the two or more sector-shaped regions and the smooth transition regions collectively make up the base arc zone.

8. The orthokeratology lens of claim 1, wherein the two or more regions of the base arc zone are irregularly shaped.

9. The orthokeratology lens of claim 8, wherein the two or more regions of the base arc zone are a first region located in the middle and a second region and a third region located on either side of the first region, and the first region, the second region and the third region collectively make up the base arc zone.

10. The orthokeratology lens of claim 8, wherein the two or more regions of the base arc zone are a first region located in the middle and a second region and a third region located on either side of the first region, the base arc zone further comprises a first smooth transition region located between the first region and the second region and a second smooth transition region located between the first region and the third region, and wherein the first region, the second region, the third region, the first smooth transition region and the second smooth transition region collectively make up the base arc zone.

11. The orthokeratology lens of claim 8, wherein the two or more regions of the base arc zone are a first region that is a part of a circular ring and a second region that has a complete circular portion in its center, and wherein the first region and the second region collectively make up the base arc zone.

12. The orthokeratology lens of claim 8, wherein the two or more regions of the base arc zone are a first region that is a part of a circular ring and a second region that has a complete circular portion in its center, the base arc zone further comprises a smooth transition region located between the first region and the second region, and wherein the first region, the second region and the smooth transition region collectively make up the base arc zone.

13. The orthokeratology lens of claim 1, wherein the base arc zone has a maximum radius of curvature of 6.0 mm to 10.5 mm, and preferably 7.0 mm to 10.0 mm.

14. The orthokeratology lens of claim 1, wherein the base arc zone has a minimum radius of curvature of 5.51 mm to 10.34 mm, preferably 5.65 mm to 9.85 mm, and more preferably 6.53 mm to 9.71 mm.

15. The orthokeratology lens of claim 1, wherein the base arc zone has a diameter of 4.5 mm to 7.0 mm, preferably 5.0 mm to 6.8 mm, and more preferably 5.2 mm to 6.5 mm.

16. The orthokeratology lens of claim 1, wherein the base arc zone is circular.

17. The orthokeratology lens of claim 1, wherein the base arc zone is elliptical.

18. A method for making an orthokeratology lens comprising an inner surface facing a cornea of a human eye when the orthokeratology lens is worn and an outer surface opposite the inner surface, the inner surface comprising a centrally located base arc zone, the method comprising the steps of:
(a) determining the maximum radius of curvature of the base arc zone;
(b) determining an amount of presbyopia correction required by the wearer;
(c) determining the minimum radius of curvature of the base arc zone using the following equation:

$$\frac{1000*(n-1)}{R1} + \Delta T = \frac{1000*(n-1)}{R2}$$

where n is a refractive index of the cornea, R1 is the maximum radius of curvature of the base arc zone in millimeters, $\Delta T$ is the determined amount of presbyopia correction required by the wearer in D (diopter), R2 is the minimum radius of curvature of the base arc zone in millimeters; and (d) making an orthokeratology lens such that the base arc zone comprises two or more regions, and such that a first region of the two or more regions has the maximum radius of curvature and a second region of the two or more regions has the minimum radius of curvature.

19. The method of claim 18, wherein step (a) comprises:
(a1) determining a refractive index of the cornea;
(a2) determining an original radius of curvature of an anterior surface of the cornea of the wearer;
(a3) determining an amount of ametropia correction required by the wearer;
(a4) determining the maximum radius of curvature of the base arc zone using the following equation:

$$\frac{1000*(n-1)}{R} + \Delta K = \frac{1000*(n-1)}{R1}$$

where n is the determined refractive index of the cornea, R is the determined original radius of curvature of the anterior surface of the cornea of the wearer in millimeters, $\Delta K$ is the determined amount of ametropia correction in D (diopter), and R1 is the maximum radius of curvature of the base arc zone in millimeters.

20. The method of claim 18, wherein the method further comprises the steps of:
(e) determining a mid-range additional refractive power required by the wearer;
(f) determining an intermediate radius of curvature of the base arc zone using the following equation:

$$\frac{1000*(n-1)}{R1} + \Delta T' = \frac{1000*(n-1)}{R3}$$

where n is a refractive index of the cornea, R1 is the determined maximum radius of curvature of the base arc zone in millimeters, $\Delta T'$ is the determined mid-range additional refractive power in D (diopter), and R3 is the intermediate radius of curvature of the base arc zone in millimeters; and wherein
the step (d) further comprises making the orthokeratology lens such that a third region of the two or more regions has the intermediate radius of curvature.

21. The method of claim 20, wherein step (e) comprises determining the mid-range additional refractive power required by the wearer using the following equation:

$$\Delta T' = \frac{1000}{M'}$$

where $\Delta T'$ is the mid-range additional refractive power required by the wearer in D (diopter), namely the amount of presbyopia correction required for mid-range vision, and M' is a visual distance for mid-range vision of the wearer on the basis of appropriate correction of far vision in millimeters.

22. The method of claim 18, wherein step (b) comprises determining the amount of presbyopia correction required by the wearer using the following equation:

$$\Delta T = \frac{1000}{M}$$

where ΔT is the amount of presbyopia correction required by the wearer in D (diopter), and M is the nearest distance that the wearer can achieve for near vision on the basis of appropriate correction of far vision in millimeters.

23. An orthokeratology lens comprising an inner surface facing a cornea of a human eye when the orthokeratology lens is worn and an outer surface opposite the inner surface, the inner surface comprising a centrally located base arc zone, wherein the base arc zone comprises a centrally located circular first region, a circular ring shaped second region surrounding the first region, and a third region surrounding the second region, wherein a radius of curvature of the second region is smaller than a radius of curvature of the first region, and the radius of curvature of the second region is smaller than a radius of curvature of the third region, wherein the radii of curvature of the first region and the second region satisfy the following relationship:

$$0.5 \leq 337.5 * \left(\frac{1}{R_B} - \frac{1}{R_A}\right) \leq 6.0$$

where $R_A$ is the radius of curvature of the first region in millimeters and $R_B$ is the radius of curvature of the second region in millimeters.

24. The orthokeratology lens of claim 23, wherein the first region and the third region have the same radius of curvature.

25. The orthokeratology lens of claim 23, wherein the radii of curvature of the first region and the third region are 6.0 mm to 10.5 mm, and preferably 7.0 mm to 10.0 mm.

26. The orthokeratology lens of claim 23, wherein the radius of curvature of the second region is 5.42 mm to 10.34 mm, and preferably 6.22 mm to 9.85 mm.

27. The orthokeratology lens of claim 23, wherein the base arc zone is circular.

28. The orthokeratology lens of claim 27, wherein the base arc zone has a diameter of 4.5 mm to 8.0 mm, preferably 5.0 mm to 7.0 mm, and more preferably 5.2 mm to 6.5 mm.

29. The orthokeratology lens of claim 27, wherein the first region has a diameter of 0.50 mm to 1.75 mm, preferably 0.50 mm to 1.5 mm, and more preferably 1.0 mm.

30. The orthokeratology lens of claim 27, wherein the second region has a radial width of 0.75 mm to 1.5 mm, preferably 1.0 mm to 1.25 mm, and more preferably 1.0 mm.

31. The orthokeratology lens of claim 27, wherein the third region has a radial width of 0.75 mm to 3.0 mm, preferably 1.0 mm to 2.0 mm, and more preferably 1.0 mm to 1.75 mm.

32. The orthokeratology lens of claim 23, wherein the base arc zone is elliptical.

33. The method of claim 19, wherein the method further comprises the steps of:
(e) determining a mid-range additional refractive power required by the wearer;
(f) determining an intermediate radius of curvature of the base arc zone using the following equation:

$$\frac{1000*(n-1)}{R1} + \Delta T' = \frac{1000*(n-1)}{R3}$$

where n is a refractive index of the cornea, R1 is the determined maximum radius of curvature of the base arc zone in millimeters, ΔT' is the determined mid-range additional refractive power in D (diopter), and R3 is the intermediate radius of curvature of the base arc zone in millimeters; and wherein the step (d) further comprises making the orthokeratology lens such that a third region of the two or more regions has the intermediate radius of curvature.

34. The method of claim 19, wherein step (b) comprises determining the amount of presbyopia correction required by the wearer using the following equation:

$$\Delta T = \frac{1000}{M}$$

where ΔT is the amount of presbyopia correction required by the wearer in D (diopter), and M is the nearest distance that the wearer can achieve for near vision on the basis of appropriate correction of far vision in millimeters.

* * * * *